United States Patent [19]
Green et al.

[11] Patent Number: 5,653,373
[45] Date of Patent: Aug. 5, 1997

[54] ARCUATE APPARATUS FOR APPLYING TWO-PART SURGICAL FASTENERS

[75] Inventors: David T. Green, Westport; Henry Bolanos, East Norwalk; Robert J. Geiste, Milford, all of Conn.; Wayne P. Young, Brewster, N.Y.; Stephen W. Gerry, Bethel; Frank M. Rende, III, Stamford, both of Conn.

[73] Assignee: United States Surgical Corporation, Norwalk, Conn.

[21] Appl. No.: 342,323

[22] Filed: Nov. 18, 1994

Related U.S. Application Data

[62] Division of Ser. No. 898,801, Jun. 15, 1992, Pat. No. 5,379,933, which is a division of Ser. No. 692,177, Apr. 26, 1991, Pat. No. 5,156,315, which is a continuation-in-part of Ser. No. 583,867, Sep. 17, 1990, abandoned.

[51] Int. Cl.$^6$ ............................................. A61B 17/10
[52] U.S. Cl. ........................ 227/175.1; 227/176.1; 227/19; 227/182.1
[58] Field of Search .................. 227/175.1–182.1, 227/19; 606/139

[56] References Cited

U.S. PATENT DOCUMENTS

| | | |
|---|---|---|
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,499,591 | 3/1970 | Green . |
| 3,545,444 | 12/1970 | Green . |

(List continued on next page.)

FOREIGN PATENT DOCUMENTS

| | | |
|---|---|---|
| 1235035 | 4/1988 | Canada . |
| 511939 | 4/1978 | U.S.S.R. . |
| 1011116 | 4/1983 | U.S.S.R. . |

*Primary Examiner*—Michael Buiz
*Assistant Examiner*—Mark Leonardo

[57] ABSTRACT

Apparatus is disclosed for applying surgical fasteners to body tissue along an arcuate path. Each surgical fastener may be in the form of a two-part fastener having a pronged fastener portion for piercing body tissue, and an apertured retainer dimensioned and configured for engaged reception of the pronged fastener portion in interference fit therewith for gripping the body tissue therebetween. Alternatively, the fasteners may be in the form of deformable staples. The apparatus preferably includes an arcuately shaped member for holding a plurality of the fastener portions in generally aligned relation, a correspondingly arcuately shaped member spaced from the fastener portion holding member for gripping body tissue therebetween and for releasably holding a plurality of the retainers in generally aligned relation and positioned opposite the fasteners when the body tissue is positioned therebetween. A fastener driver is provided for sequentially advancing the pronged fastener portions toward the apertured retainers to cause the fastener portions to pierce the body tissue therebetween. A knife may be provided to cut the body tissue adjacent the fasteners as the fasteners are applied.

47 Claims, 19 Drawing Sheets

U.S. PATENT DOCUMENTS

| | | |
|---|---|---|
| 3,665,924 | 5/1972 | Noiles et al. . |
| 3,675,688 | 7/1972 | Bryan et al. . |
| 3,735,762 | 5/1973 | Bryan et al. . |
| 3,740,994 | 6/1973 | DeCarlo, Jr. . |
| 3,780,416 | 12/1973 | Rider . |
| 3,844,289 | 10/1974 | Noiles . |
| 4,429,695 | 2/1984 | Green . |
| 4,473,077 | 9/1984 | Noiles et al. . |
| 4,488,523 | 12/1984 | Shichman ............................ 227/179.1 |
| 4,500,024 | 2/1985 | DiGiovanni et al. . |
| 4,506,670 | 3/1985 | Crossley . |
| 4,520,817 | 6/1985 | Green . |
| 4,523,707 | 6/1985 | Blake, III et al. . |
| 4,527,724 | 7/1985 | Chow et al. . |
| 4,556,058 | 12/1985 | Green . |
| 4,566,620 | 1/1986 | Green et al. . |
| 4,569,346 | 2/1986 | Poirier . |
| 4,576,165 | 3/1986 | Green et al. . |
| 4,576,167 | 3/1986 | Noiles ................................ 227/179.1 |
| 4,589,416 | 5/1986 | Green . |
| 4,606,343 | 8/1986 | Conta et al. . |
| 4,606,345 | 8/1986 | Dorband et al. . |
| 4,608,981 | 9/1986 | Rothfuss et al. . |
| 4,610,383 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,863,088 | 9/1989 | Redmond et al. . |
| 4,881,544 | 11/1989 | Green et al. . |
| 4,930,674 | 6/1990 | Barak . |
| 4,932,960 | 6/1990 | Green et al. . |
| 4,938,408 | 7/1990 | Bedi et al. . |
| 5,065,929 | 11/1991 | Schulze et al. . |
| 5,083,695 | 1/1992 | Foslien et al. . |
| 5,106,008 | 4/1992 | Tompkins et al. . |
| 5,129,570 | 7/1992 | Schulze et al. . |
| 5,141,144 | 8/1992 | Foslien et al. . |

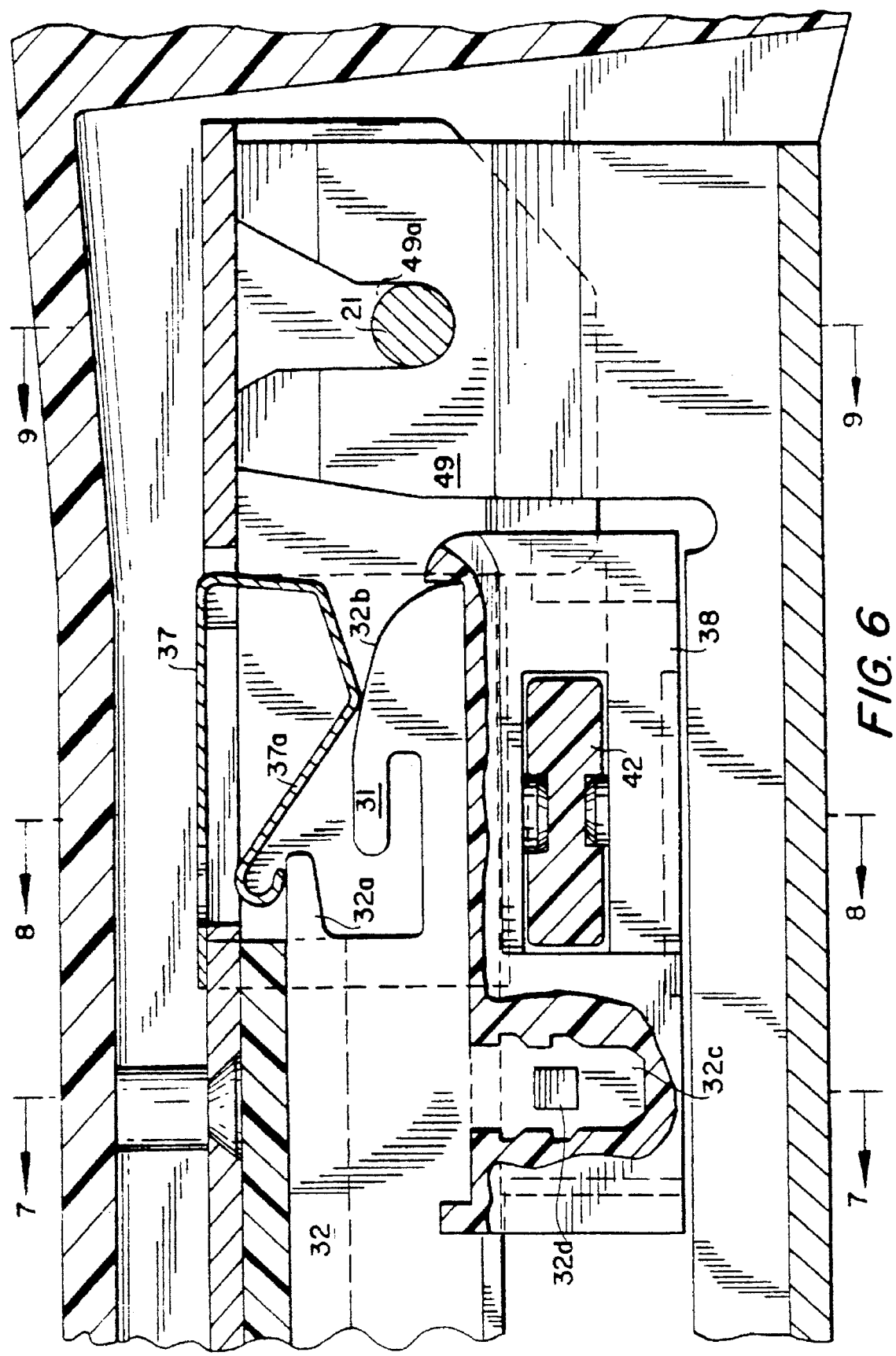

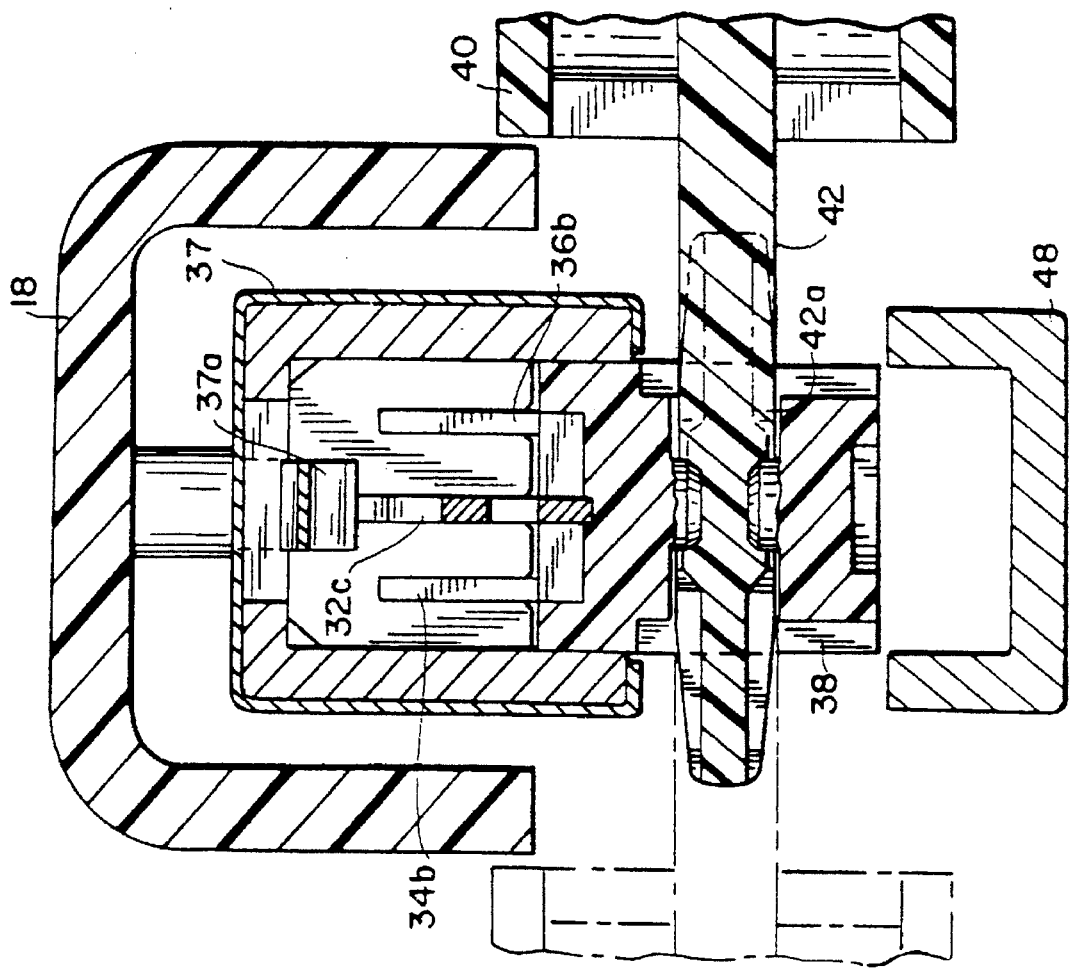
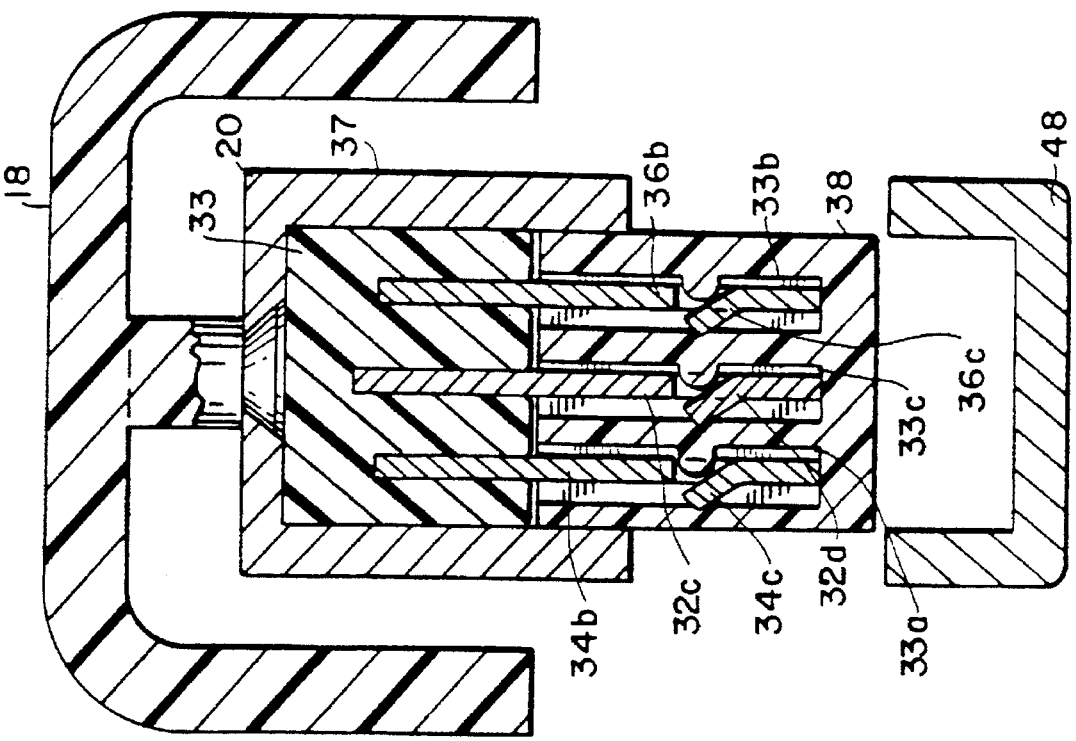

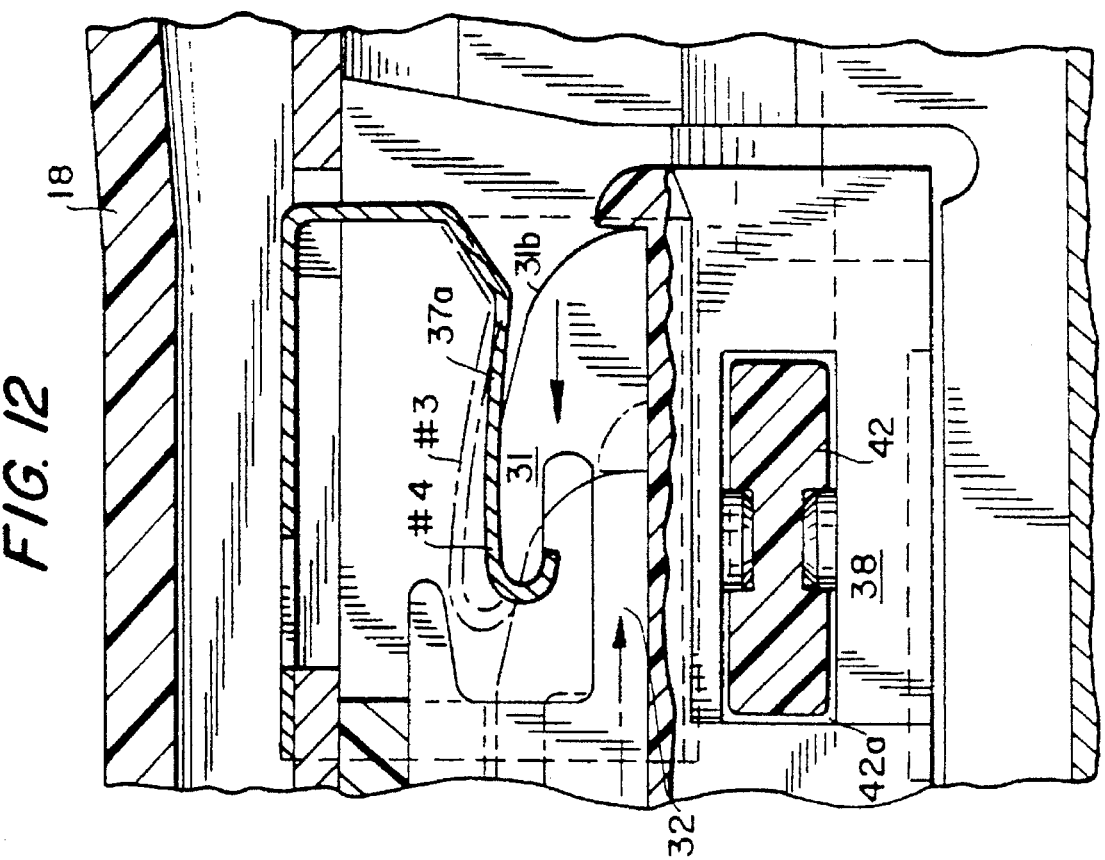
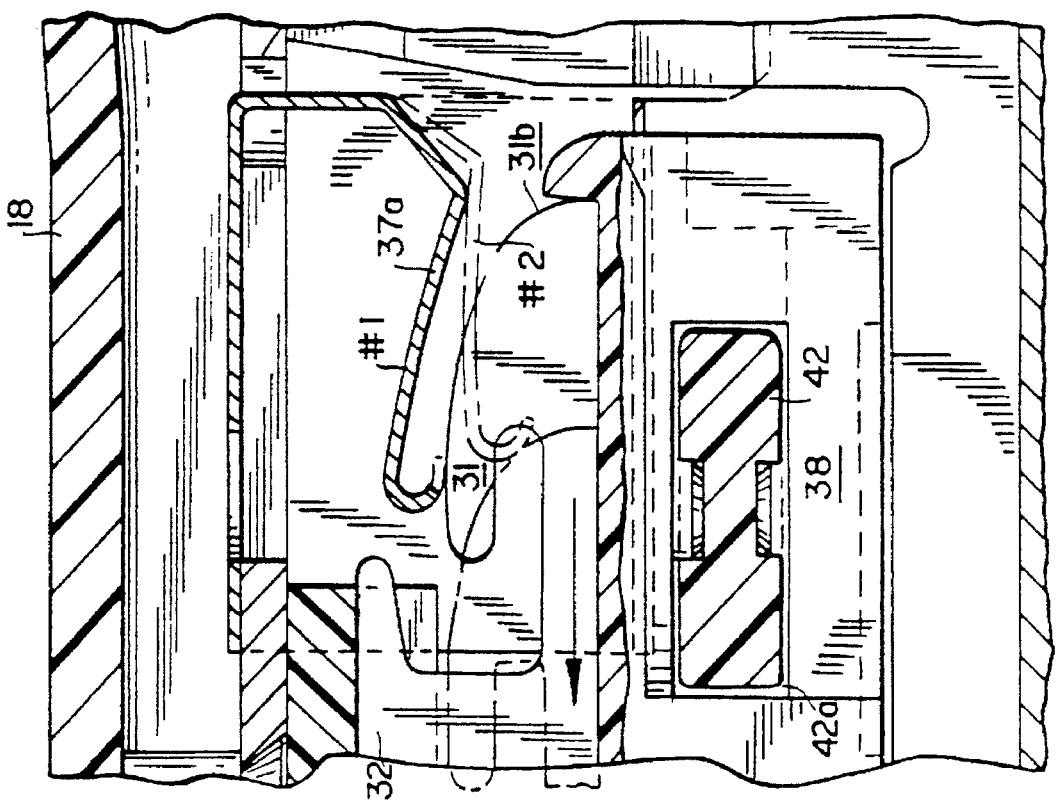

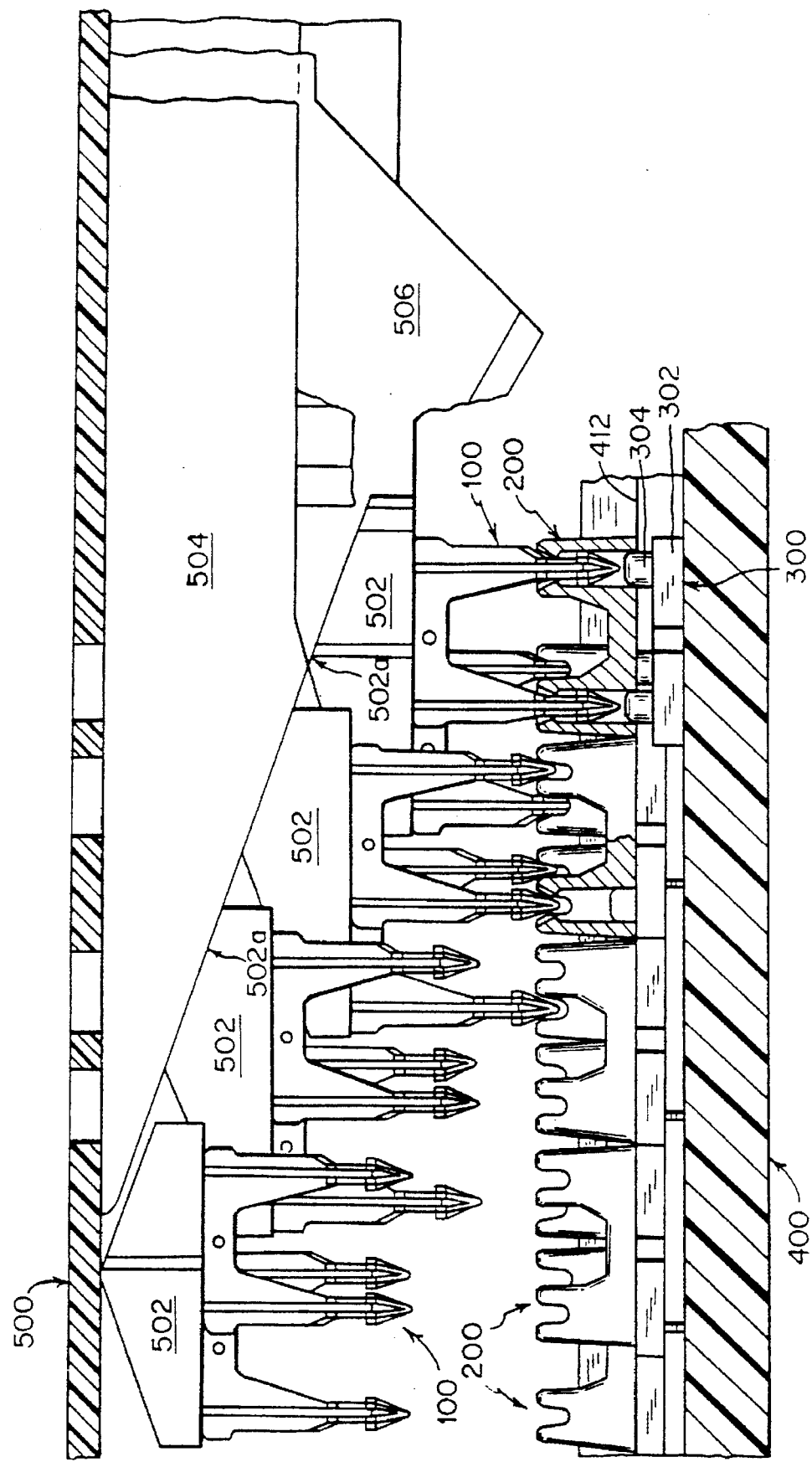

ARCUATE APPARATUS FOR APPLYING TWO-PART SURGICAL FASTENERS

CROSS REFERENCE TO RELATED APPLICATIONS

This is a divisional of U.S. application Ser. No. 07/898,801, filed Jun. 15, 1992, now U.S. Pat. No. 5,379,933, which is a divisional of U.S. application Ser. No. 07/692,177, filed Apr. 26, 1991, now U.S. Pat. No. 5,156,315, which is a continuation-in-part of application Ser. No. 07/583,867, filed Sep. 7, 1990, now abandoned.

BACKGROUND OF THE INVENTION

1. Field of the Invention

This invention relates to an apparatus for applying surgical fasteners along an arcuate path in bodily areas otherwise difficult to reach with straight line fastener apparatus. More particularly, the invention relates to a fastener applying apparatus having an improved arcuately configured fastener cartridge and holder for the retainer portion of two-part surgical fasteners.

2. Background of the Prior Art

In some surgical operations it is necessary to fasten body tissue or to adjoin two hollow body organs alongside each other, with their longitudinal axes positioned generally parallel to each other, and to effect a longitudinal cut through the contacting circumferential walls of the two organs in order to open them to each other. After joining the two organs essentially constitute a single hollow chamber along the length of the cut. Correspondingly, the circumferential portions of the two adjoining organs on each lateral side of the cut must be sutured by at least one line of "stitches" in order to maintain the integrity of the union.

Instruments for this purpose are known in the art, and are described in U.S. Pat. Nos. 3,079,606, 3,490,675 and 3,499,591. Such instruments are generally referred to as linear cutting staplers and include two elongate fingers which are respectively insertable into the tissue or into each organ from an open end thereof such that the two fingers have the adjoining walls of the adjacent organs therebetween. Further examples of such instruments are disclosed in commonly assigned U.S. Pat. Nos. 4,429,695 and 4,520,817. The disclosures of these two last mentioned patents are incorporated herein by reference.

One of the fingers includes a disposable cartridge carrying a plurality of staples arranged in at least two lateral rows while the other finger includes an anvil for curling the staple legs into hook form upon being driven against the anvil. The stapling operation is effected by a pusher device which travels longitudinally along the cartridge carrying finger extending into one organ. The pusher mechanism acts simultaneously upon the staples at corresponding longitudinal positions in each lateral row, but successively acts upon the staples along the rows. For example, if two lateral rows of staples are provided, each row comprising twenty staples, the pusher means acts upon two staples at a time, one in each row, and successively acts upon each succeeding pair of staples.

Immediately behind the pusher means and laterally positioned between the staple rows is a knife member which severs the tissue or the facing adjoining walls of the two organs to thereby longitudinally open the two organs to each other between the rows of staples.

Up to the present these devices were limited to applying metal staples by means of a straight device which applies the fasteners along two or more straight line paths. For example, the apparatus disclosed in U.S. parent application Ser. No. 07/583,867 is a straight device. Two-part absorbable fasteners, such as those used in devices described in U.S. Pat. No. 4,665,916, hereby incorporated by reference, have been limited to devices which apply all of the fasteners simultaneously. Indeed, the retainer members of such absorbable fastener devices typically have been constructed as a web of retainers interconnected by flexible or frangible members. See, for example, U.S. Pat. No. 4,589,416. Devices of the type shown in the aforementioned U.S. Pat. Nos. 3,079,606; 3,490,675 and 3,499,591, on the other hand, employ an actuating cam bar which travels substantially perpendicularly to the direction of fastener motion to effect sequential placement of staples.

The advantage of applying fasteners while cutting adjacent tissue by curved devices to reach normally inaccessible portions of the body is clear. However, up to the present, the application of fasteners in the form of either deformable staples or two-part absorbable fasteners, accompanied by cutting, has been limited to straight instruments. In particular, maintaining the precise dimensional relation between components and providing accurate and precise spacing is peculiarly difficult with a curved apparatus. In addition, fasteners of the two-part type, i.e. fastener and retainer, present further difficulties and complications because of the need to provide precise alignment and movement of the fastener parts, an objective which has proved difficult even on straight devices.

The present invention relates to an apparatus which successfully combines a system of applying fasteners sequentially along an arcuate path while effecting complete closures in areas of the body previously inaccessible. Moreover, the present invention is applicable to fastener operations with and without cutting, while incorporating safety features which prevent unwanted movement of certain designated components during actuation of the apparatus.

SUMMARY OF THE INVENTION

An apparatus for applying at least one row of surgical fasteners is provided which comprises first arcuate means for holding the fasteners, second arcuate means configured and dimensioned to cooperate with said arcuate fastener holding means, and means for driving the fasteners into tissue toward the second arcuate means. Closure of the fastener may be effected by suitable means. For example, for two-part fasteners, retainers are provided; for fasteners in the form of staples, leg deforming anvils are provided.

In one preferred embodiment, two-part fasteners are contemplated. The apparatus is adapted for applying at least one row of two-part surgical fasteners, each surgical fastener having a pronged fastener portion and a retainer. Arcuate means is provided for holding the fastener portions of the two-part surgical fasteners. An arcuately configured retainer cartridge includes means for holding a plurality of retainers in positions opposite the fastener portions, and a plurality of retainer mounting elements are located in the arcuately configured retainer cartridge for releasably engaging and holding the retainers. The fastener portions and retainers are arranged in general alignment with the arcuate axis of the apparatus, and the fastener portions are preferably sequentially driven into engagement with their respective retainers. Means for sequentially driving the fastener portions of the two-part fasteners into engagement with the respective opposed retainers is also provided.

The retainer mounting elements are slidably mounted within a lower channel in the arcuately configured retainer cartridge and arranged to release their respective retainers in response to the engagement of the fastener portions with their respective retainers. Further, the retainer mounting elements each comprise a base portion and at least one upright post for engaging an aperture in the retainer and frictionally holding the retainer.

The retainer mounting elements may be arcuately configured similar to the cartridge, or depending upon relative dimensions, they may be straight without adversely affecting their movements.

A surface portion of the upright post is preferably inclined on at least one vertical side and backstop means is provided for bracing the retainers when engaging with the fastener portions. The backstop means comprises a horizontal shelf portion of the cartridge upon which the retainers at least partially rest. The lower and upper channels have vertical sidewalls, and the lower channel is of lesser width than the upper channel and is located below the upper channel thereby forming at least one shelf portion. The lower channel has a plurality of vertical guide rails and the retainer mounting elements each have at least one vertical notch for cooperating with a respective one of the vertical guide rails. Preferably the two-part surgical fasteners are bio-absorbable and the apparatus is adapted to fasten body tissue therewith.

The preferred embodiment of the apparatus comprises a two-part frame having separable sections capable of releasable attachment to each other and each having an elongated finger portion. A curved fastener carrying cartridge is mounted along one of the finger portions and carries a plurality of the fastener portions, and a similarly curved retainer carrying cartridge is mounted along the other finger portion opposite the fastener cartridge and carries a plurality of the retainer members positioned opposite the fastener portions. A pair of similarly curved cam bars are positioned for slidable movement distally and proximally within the frame for sequential engagement with the fastener pushers. A handle is positioned at the proximal end and the cartridges and supporting structure extend from the handle toward the distal end. The cartridge structures may curve to the left, or to the right, or up, or down from the handle to the distal end, depending upon the intended application.

A generally U-shaped shoe plate is provided between each fastener and retainer cartridge and the respective channel members of the frame. Each shoe plate defines a channel for reception of a respective shoe associated with the cam bars. The respective shoes prevent separation of the frame members when the curved cam bars are advanced a predetermined distance due to the entry of the shoes associated therewith into the channels defined by the shoe plates.

Broadly the invention relates to an apparatus for applying fasteners of various types to body tissue, including two-part fasteners having a fastener portion and a retainer, staples which have deformable legs, and the like. For either type of fastener apparatus, a two-part apparatus broadly includes a system for preventing separation of the parts after firing of the fasteners has begun. Also, prevention of cutting body tissue after the apparatus has fired the fasteners is provided. In addition, a system for holding the retainers of two-part fasteners for driving the fastener portions toward the body tissue and the retainers while facilitating engaged reception of the fastener portions is also disclosed. The apparatus may also include a manually operable pad which is removably attached to advancement means for driving-the fasteners. The pad is insertable into different sides of the advancement means to provide versatility to the user.

A method is disclosed for applying at least one row of fasteners along an arcuate path, comprising holding the fasteners in arcuately configured holding means, and advancing the fasteners toward means adapted to cooperate with the fastener holding means to drive the fasteners into body tissue.

Also disclosed is a method for applying at least one row of two-part surgical fasteners, each surgical fastener having a pronged fastener portion and a retainer. The method comprises holding the fastener portions of the two-part surgical fasteners in arcuately configured fastener holding means, releasably holding a plurality of retainers in arcuately configured retainer holding means in positions opposite the fastener portions, and driving the fastener portions of the two-part fasteners into engagement with their respective opposed retainers.

In one preferred embodiment, a method is disclosed for applying at least one row of two-part surgical fasteners with arcuately configured fastener holding means, each surgical fastener having a pronged fastener portion and a retainer, comprising holding the fastener portions of the two-part surgical fasteners, releasably holding a plurality of retainers in arcuately configured retainer holding means in positions opposite the fastener portions, and sequentially driving the fastener portions of the two-part fasteners into engagement with their respective opposed retainers. Each surgical fastener has a pronged, generally u-shaped fastener portion, and an apertured retainer dimensioned for engaged reception of the fastener portion. Preferably the method comprises holding a plurality of the fastener portions, releasably holding a plurality of the retainers in positions opposite the fastener portions such that the apertures thereof face the pronged portions of the fastener portions, and sequentially driving the fastener portions of the two-part fasteners toward the retainers so as to cause the pronged portions to be engagably received within the apertures of the retainers. Preferably two rows of fastener portions and mating retainers are provided.

According to the method, body tissue to be fastened is positioned between the rows of fastener portions and retainers such that sequentially driving the fastener portions toward the retainers causes the fastener portions to be driven through the tissue so as to grip the tissue between the fastener portions and the retainers. The method further comprises cutting the tissue while driving the fastener portions toward the retainers.

The method is preferably accomplished on a curved apparatus which permits release of the tissue after the fastening and engagement of the two-part fasteners is complete.

A system for holding the fastener portions of two-part fasteners to be applied along an arcuate path is disclosed whereby the fastener portions are engagably received by the retainer portions after being applied to body tissue.

The curved apparatus of the invention is configured to reach areas of the body difficult to reach with straight instruments; in some instances impossible to reach. The instrument and method are of particular use in vaginal hysterectomies, tubal ligations, colon surgery, etc.

BRIEF DESCRIPTION OF THE DRAWINGS

Preferred embodiments of the invention are described hereinbelow with reference to the drawings wherein:

FIG. 3A is a view of an alternative embodiment of the fasteners of FIG. 3, provided in the form of a string of fasteners connected by frangible connectors;

FIG. 6 is a cross-sectional view taken along lines 6—6 of FIG. 1 illustrating the safety locking mechanism for preventing movement of the cam bars and tissue cutting knife after application of the fastener;

FIG. 7 is a cross-sectional view taken along lines 7—7 of FIG. 6 illustrating a part of the finger operated advancement mechanism for cutting tissue and effecting closure;

FIG. 8 is a cross-sectional view taken along lines 8—8 of FIG. 6 illustrating the reversible finger pad for advancement of the tissue cutting knife and effecting fastener closure;

FIG. 11 is a cross-sectional view of the safety locking mechanism shown in FIG. 6 in two sequential positions after initial distal movement of the fastener closure mechanism;

FIG. 12 is a cross-sectional view of the safety locking mechanism after the fastener closure mechanism has been returned to the proximal position;

FIG. 22 illustrates in cross-sectional view, the two-part surgical fasteners being joined in the apparatus of the present invention.

DETAILED DESCRIPTION OF THE PREFERRED EMBODIMENTS

Figure 1:
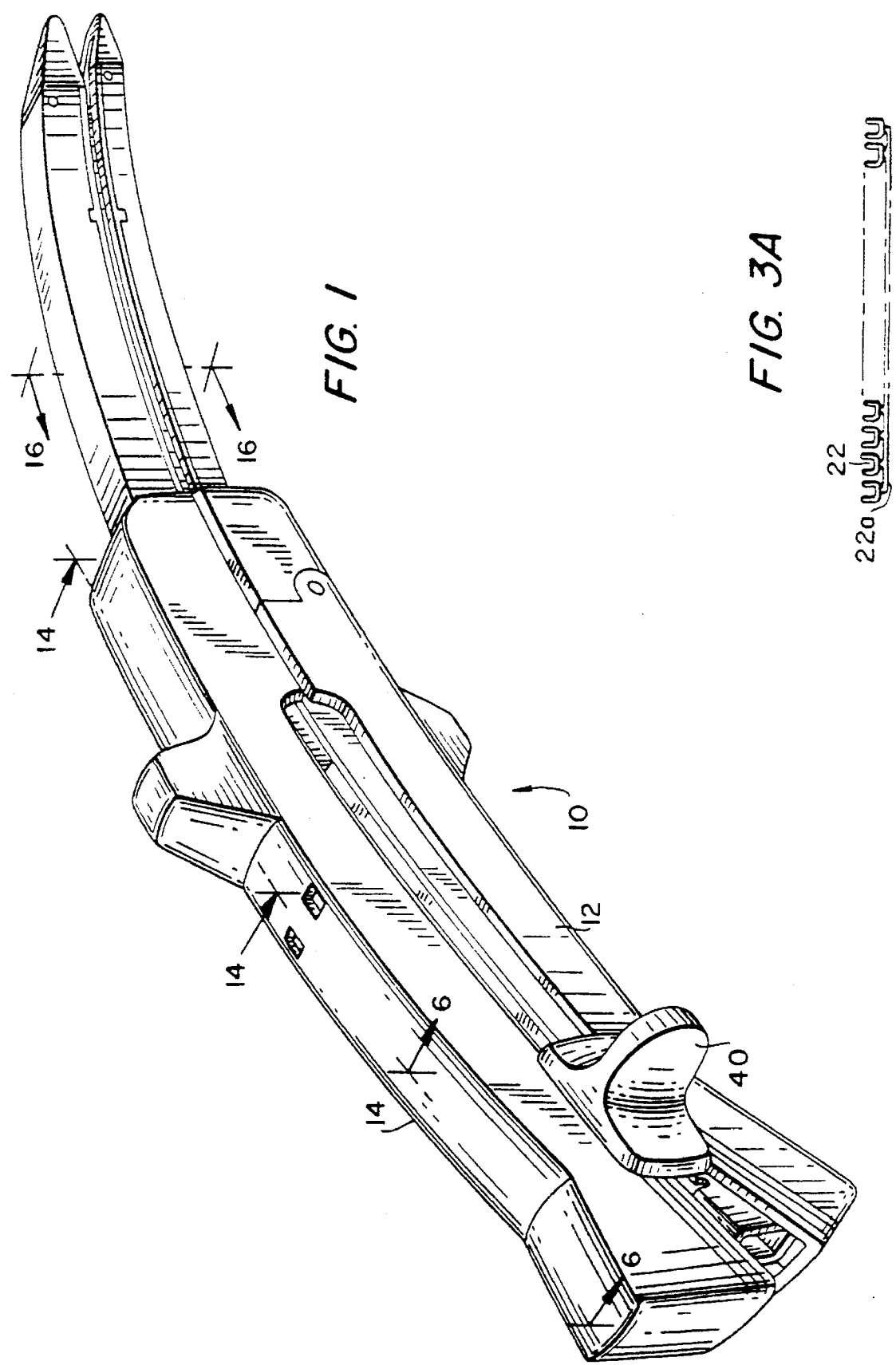
FIG. 1 is a perspective view of the arcuately configured apparatus for applying two-part surgical fasteners constructed according to the present invention.

Referring initially to FIG. 1, there is illustrated a perspective view of the curved apparatus 10 for applying two-part fasteners constructed according to the present invention. The apparatus shown is curved to the right from the handle to the distal end. Alternatively, the apparatus may be curved to the left or optionally upward or downward from the handle to the distal end. The apparatus 10 includes half sections 12 and 14 as shown, which are adapted to be clamped together in a manner to be described. The two half sections 12 and 14 are shown in perspective view in FIG. 2 and each half section is shown with parts separated in FIGS. 3 and 4.

Figure 3:
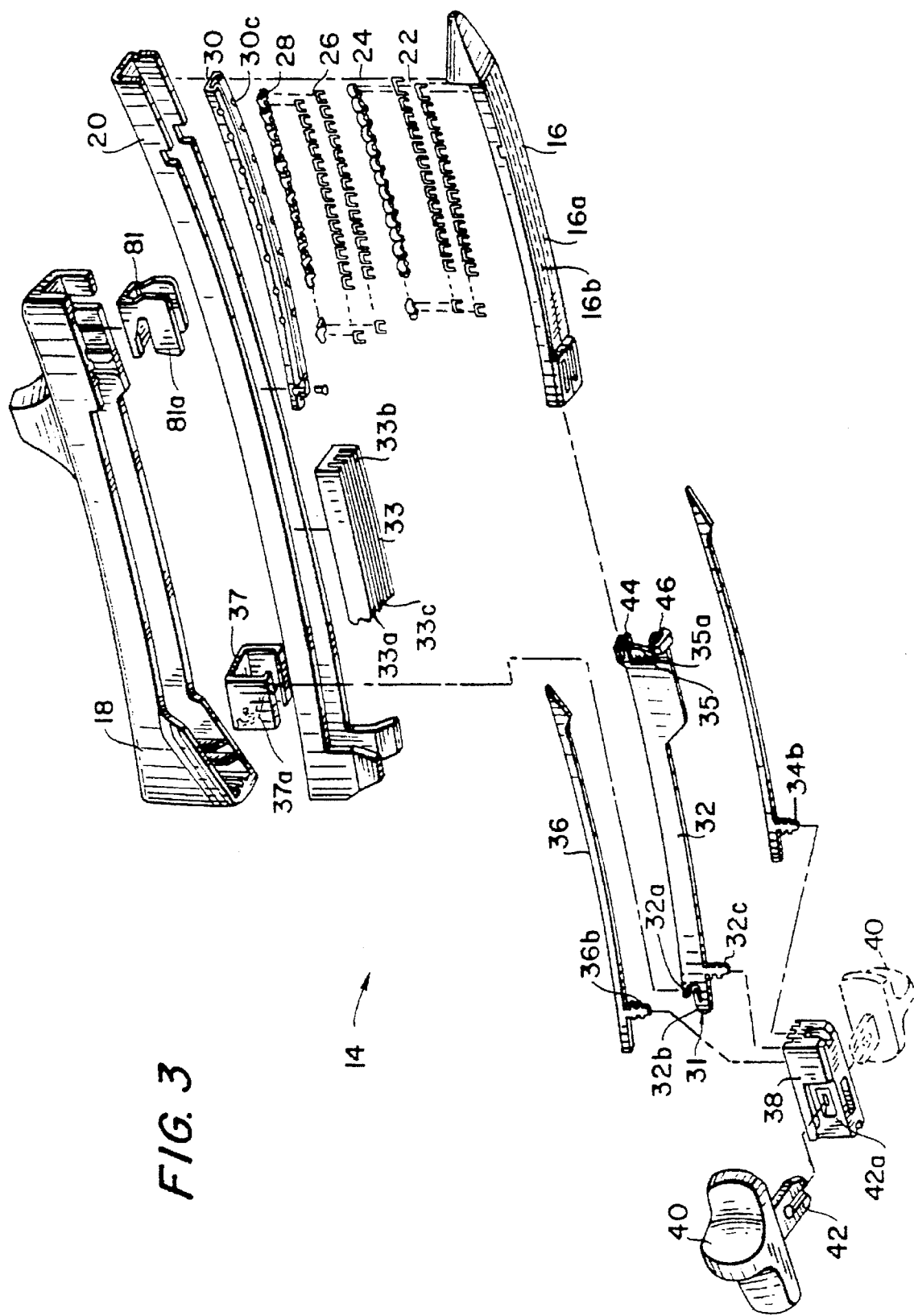
FIG. 3 is an exploded perspective view with parts separated, of the arcuately configured fastener cartridge and associated handle mechanism of the apparatus of FIG. 1.

Referring now to FIG. 3, arcuate half section 14 for receiving and supporting fastener cartridge 16 is shown. The handle section includes arcuate body 18, which receives arcuate fastener channel 20. Fastener cartridge 16 is curved to conform and to be received into fastener channel 20. This cartridge 16 receives two staggered rows of U-shaped fasteners 22, 26 which are individually upstanding and separated from each other in the embodiment of FIG. 3. In an alternative embodiment shown in FIG. 3A the fasteners are injection molded with frangible or flexible connectors 22A as shown to facilitate assembly with the cartridge 16. The connectors either break upon firing, or are sufficiently flexible to allow relative motion among the fasteners when inserted into the tissue.

A first pair of rows of fastener portions such as fasteners 22 are disposed on one side of a knife bar 32 and are provided with corresponding fastener pushers 24. A second similar string of a pair of U-shaped fasteners 26 are advanced by corresponding pushers 28 on the other side of knife bar 32. The fasteners and retainers of each row are staggered with respect to the fasteners and retainers of the next adjacent row. Fasteners 22 and 26 are maintained within suitable spaces 16a and 16b provided in arcuately shaped cartridge 16 which are dimensioned to frictionally support the fasteners until ejected by the pushers. Shoe plate 30 is provided with a similar curved configuration as shown, to fit within arcuate fastener channel 20 for slidable reception of a fastener shoe 44.

Referring further to FIG. 3, curved knife bar 32 is flanked by arcuately shaped cam bars 34 and 36 which are connected to bar retainer 38 which in turn is connected to finger pad 40 for finger operated motion of the cam bars 34, 36. Finger pad 40 is connected to bar retainer 38 by stem 42 inserted into aperture 42a. The position of finger pad 40 is reversible as shown in dotted lines at 40a by insertion of stem 42 into bar retainer 38 from the opposite side. Other means can be provided in the bar retainer 38 for releasably holding finger pad 40 to allow reversibility. This arrangement permits versatility of operation of the apparatus for instances where a right curve, left curve, upward curve or downward curve may be required. Also, the reversible finger pad is user friendly for left handed or right handed users.

Figure 4:
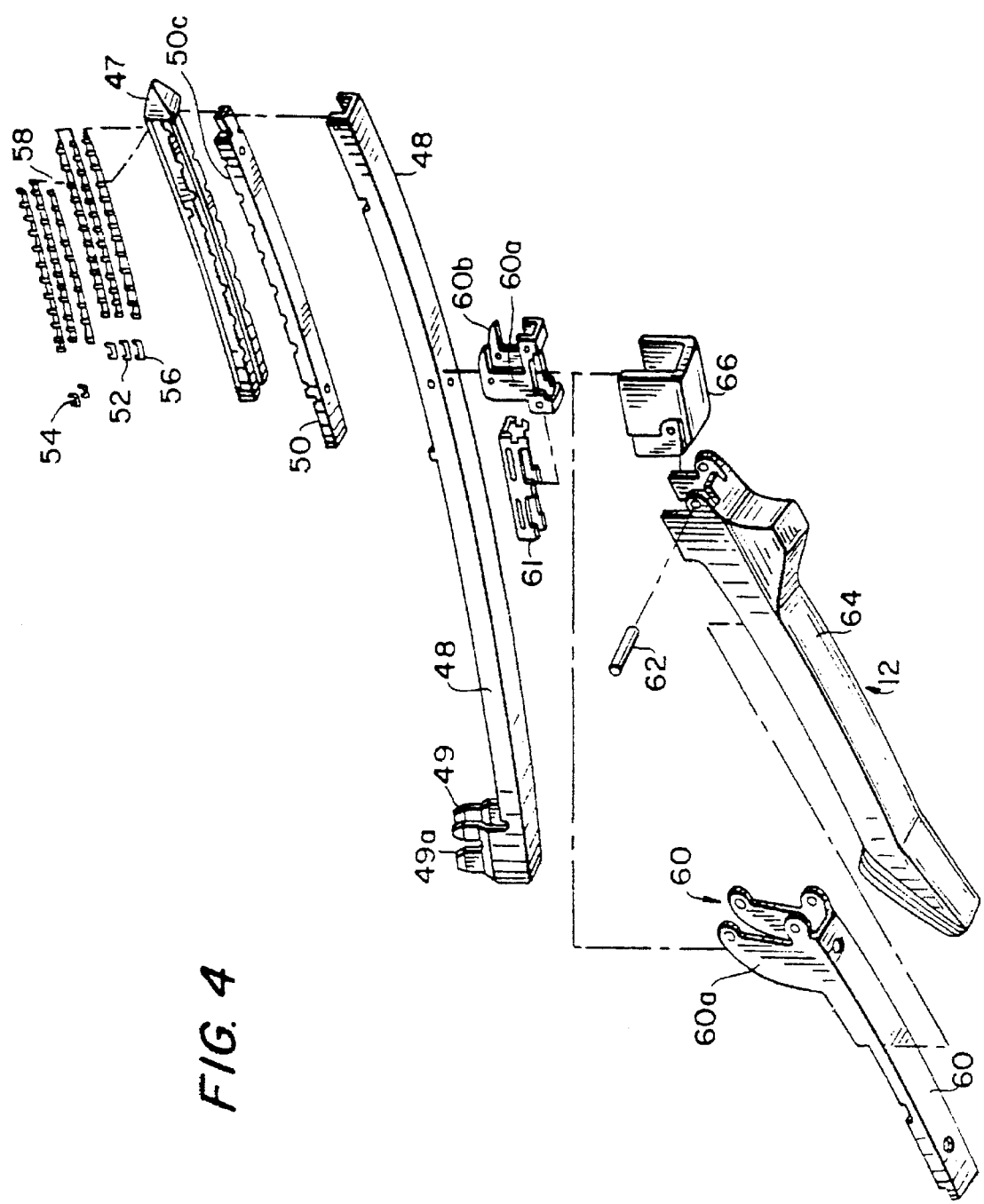
FIG. 4 is an exploded perspective view with parts separated, of the arcuately configured retainer cartridge and associated handle mechanism.
Figure 5:
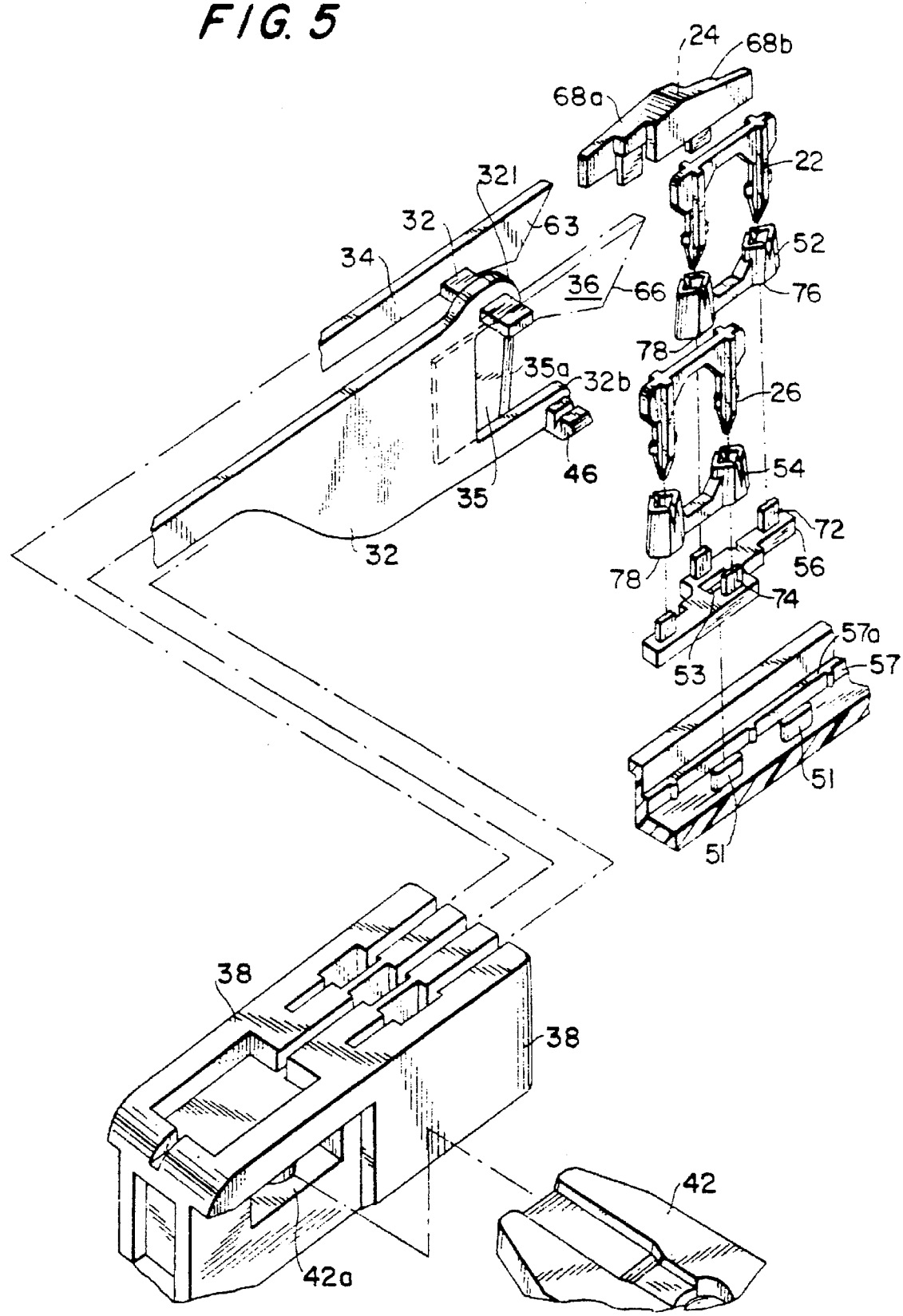
FIG. 5 is an exploded perspective view of the operable portions of the apparatus of FIG. 1, illustrating the arcuately configured mechanism for advancing camming fingers and a tissue cutting blade to secure the two-part fastener/retainer and for cutting adjacent tissue.

Fastener shoe 44 is attached to knife bar 32 at tab 32l on the fastener side and retainer shoe to is attached to knife bar 32 at tab 32b on the retainer side as shown in FIG. 5. As will be described in further detail, fastener shoe 44 and retainer shoe to slide within respective shoe plates 30,50 (FIGS. 3 and 4) and serve to help secure the two half sections 12, 14 together after the knife bar is advanced a predetermined amount in order to prevent separation of the half sections. Also, the shoes 44,46 and the respective shoe plates 30, 50 serve to control the gap between the fastener cartridge and the retainer cartridge and thus the relative positions of the fastener half section 14 and the retainer half section 12. Knife 35 having a sharp knife edge 35a is attached to knife bar 32 as shown for cutting tissue simultaneously with the fastening operation. Knife edge 35 lags the cam bars a small distance, i.e. about 5 mm. Since the entire assembly is arcuately configured to facilitate access to body areas normally impossible or difficult to reach with straight instruments, the requisite curvature of the cam bars 34, 36, the knife bar 32, the channel 20, the cartridge 16 and related components must be maintained appropriately in concentric complementary relation. The dimensions must be complementary to each other and fall within critical limits to facilitate the free and unimpeded movement of the fastener firing components as described. In this regard, molded plastic guide insert 33, disposed within fastener channel 20, provides suitable guide channels 33a, 33b and 33c for the two cam bars 34, 36 and the knife bar 32, respectively. Although only a portion of guide insert 33 is shown, the guide insert actually extends from the proximal end of the guide channel 20 to a point immediately proximal of cartridge 16 and shoe plate 30.

Referring now to FIG. 4 the arcuately configured retainer half section 12 is illustrated with parts separated. Retainer channel 48 is provided with retainer shoe plate 50 and retainer cartridge 47 for supporting two staggered rows of retainers 52 and 54, with associated retainer holders 56 and 58. The retainers are each precisely positioned opposite a respective fastener when the complementary curved half sections of the apparatus are assembled. In an alternative embodiment the retainers can be linked in the manner shown in U.S. Pat. No. 4,584,416, herein incorporated by reference, and either break or are sufficiently flexible to allow relative motion among the fasteners when inserted into the tissue.

Handle clamp 60 is pivotally attached to channel 48 via pin 62 with spring 65 (shown in FIG. 13) positioned to resiliently bias handle clamp 60 away from retainer channel 48. Handle cap 64 is attached to handle clamp 60 and nose cap 66 is provided as shown at the distal end of cap 64. The entire handle is also curved on the same radius as the channels 20, 48 and the cartridge sections.

Referring now to FIG. 5, the motion of curved knife bar 32 and associated cam bars 34,36 is illustrated. When finger pad 40 is moved distally by the surgeon, the distal sloped surfaces 63, 66 of cam bars 34,36 engage the corresponding proximal surfaces 68a and 70a (not shown in FIG. 5) of fastener pushers 24 and 28 (not shown in FIG. 5), causing movement of the pushers in a direction substantially perpendicular to movement of cam bars 34, 36 and engagement with fasteners 22 and 26. This movement follows the curve of the instrument as shown and causes the fasteners to move transversely toward corresponding retainers which are at this time, secured in upstanding relation to retainer monitoring elements shown as retainer holders 56 and 58 (holder 58 not shown in FIG. 5) by insertion of upstanding posts 72, 74 into the apertures 76, 78 on the side of retainers 52, 54 opposite the fastener side. The retainer holders 56, 58 prior to firing the fasteners, are positioned within cartridge 47 such that the top surfaces of the posts 72, 74 are approximately at the level of the surfaces 57a of the side rails 57 of retainer cartridge 47 as shown in FIGS. 5 and 16.

Figure 16:
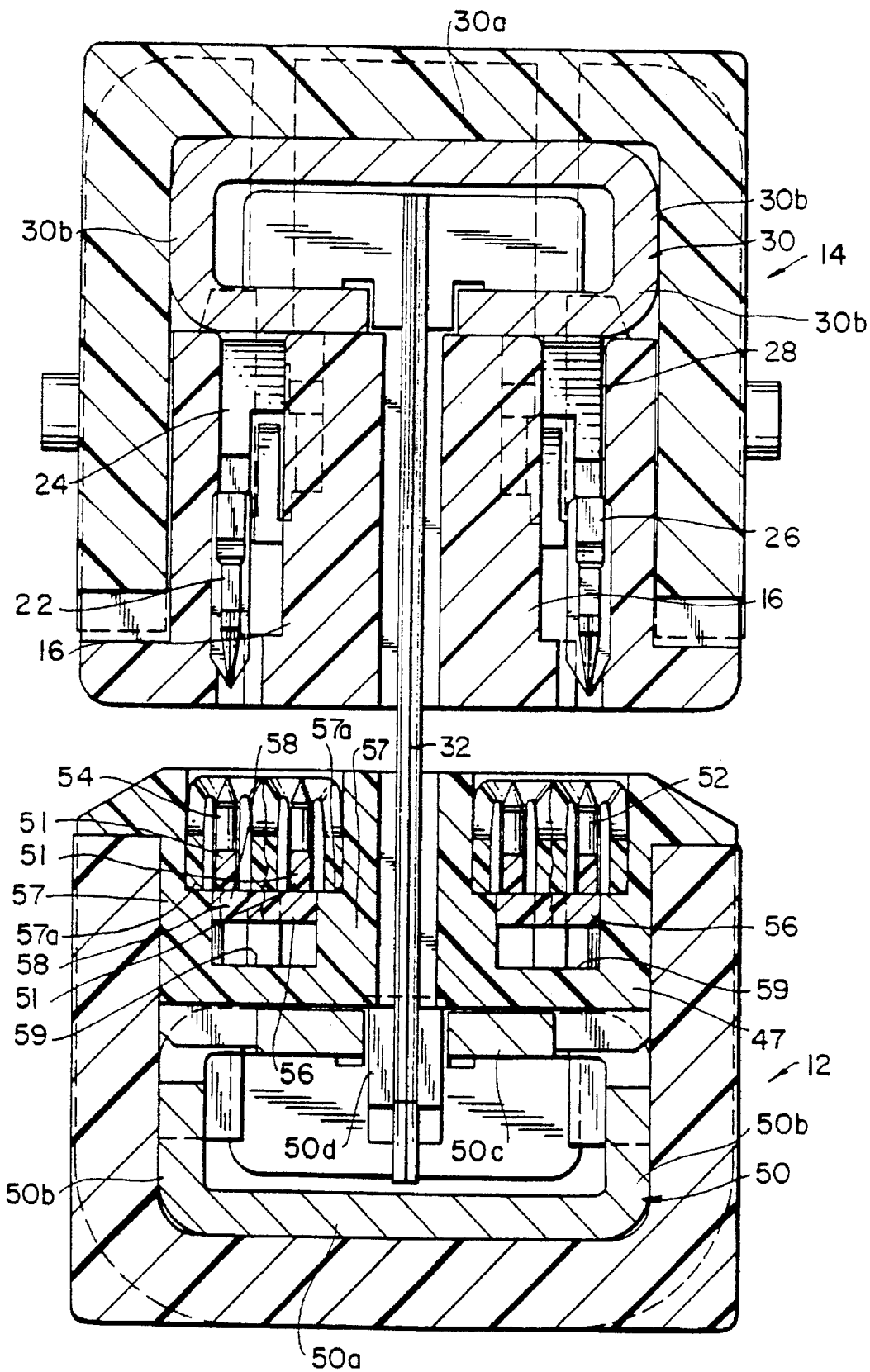
FIG. 16 is a cross-sectional view taken along lines 16—16 of FIG. 1, illustrating the relative positions of the fasteners and retainers prior to firing the apparatus.

The retainer holders 56,58 are dimensioned to be positioned between rails 57 of the cartridge 52 with slight frictional fit to maintain the position shown in FIG. 16. This position permits the movement of holder 56 toward the lower surface 59 of cartridge 52 during firing such that posts 51 enter central apertures 53 of the holders 56 to assist in continued alignment of the fastener retainers 52, 54 with the fasteners 22, 26. Additional details relating to the fasteners and retainers will be provided in conjunction with FIGS. 18–22.

Figure 10:
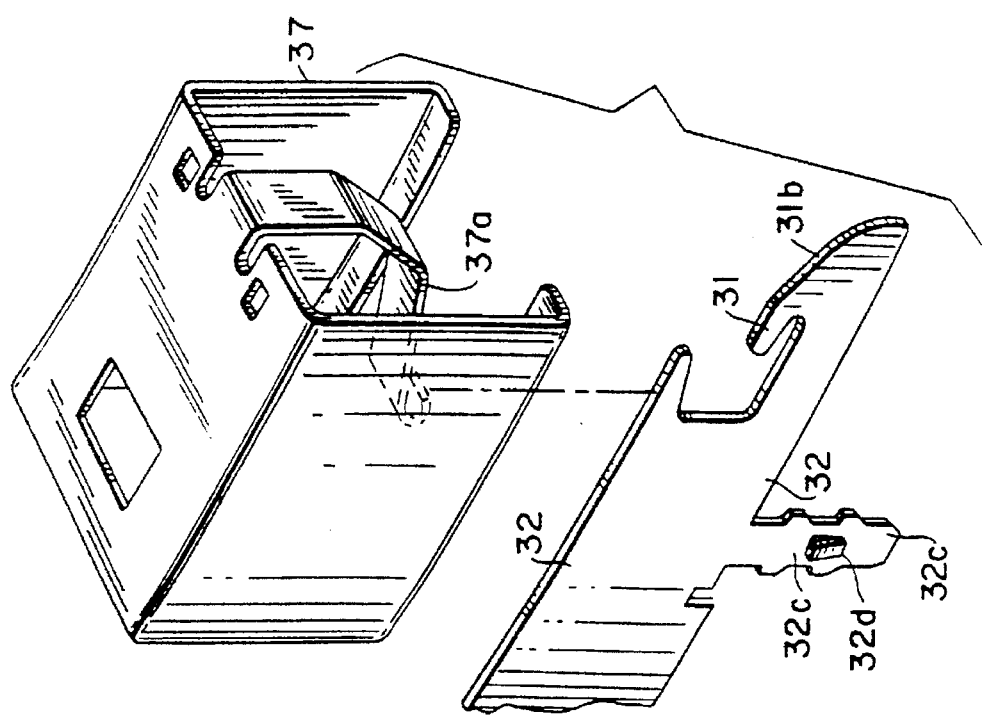
FIG. 10 is a perspective view of the safety locking mechanism shown in FIG. 6.

Referring now to FIG. 6 the single use locking feature of the present invention is illustrated. Knife bar 32 is configured at the proximal end in the form of distally facing hook 31 positioned within handle 18 is locking device 37 which incorporates resilient pivotal hook 37a (see also FIG. 10) positioned and adapted to receive the distal end portion of hook 31 to prevent further advancement of the knife bar 32 and cam bars 34, 36 after firing the fasteners and retracting the knife bar 32 to its proximal position.

FIG. 6 illustrates the relative positions of locking device 33 and knife bar hook 31 prior to firing the instrument, i.e. biased upwardly as shown, by proximally facing tongue 32a at the proximal end of knife bar 32. During the initial distal movement of knife bar 32, it is in the initial position shown and hook 37a is in the position "1" shown in FIG. 11. As the knife bar 32 moves forward to position "2" (shown dotted), hook 37a moves to position #2 in FIG. 11 while slidably engaging the curved upper surface 32b of the proximal end of knife bar 32. During the remainder of the distal movement of knife bar 32 and the subsequent firing of the fasteners, hook 37a remains in its lowermost position. After the fasteners are fired and knife bar 32 and cam bars 34, 36 are then returned (retracted) to their proximalmost positions, hook 37a receives distal facing hook 31 shown at positions "3" and "4" in FIG. 12, thereby preventing further forward movement of the knife bar 32. Thus forward movement of the knife bar 32 is prevented after the fasteners have been applied to skin tissue and the knife bar is retracted to a proximal position, thereby preventing the user from cutting tissue inadvertently by firing an empty fastener cartridge. Since apparatus 10 is normally intended for use in surgical procedures to organs and other internal body portions, creating an incision in such organs without application of fasteners will have serious adverse consequences. The possibility of such adverse consequences occurring is thus eliminated in the curved apparatus of the present invention.

Figure 9:
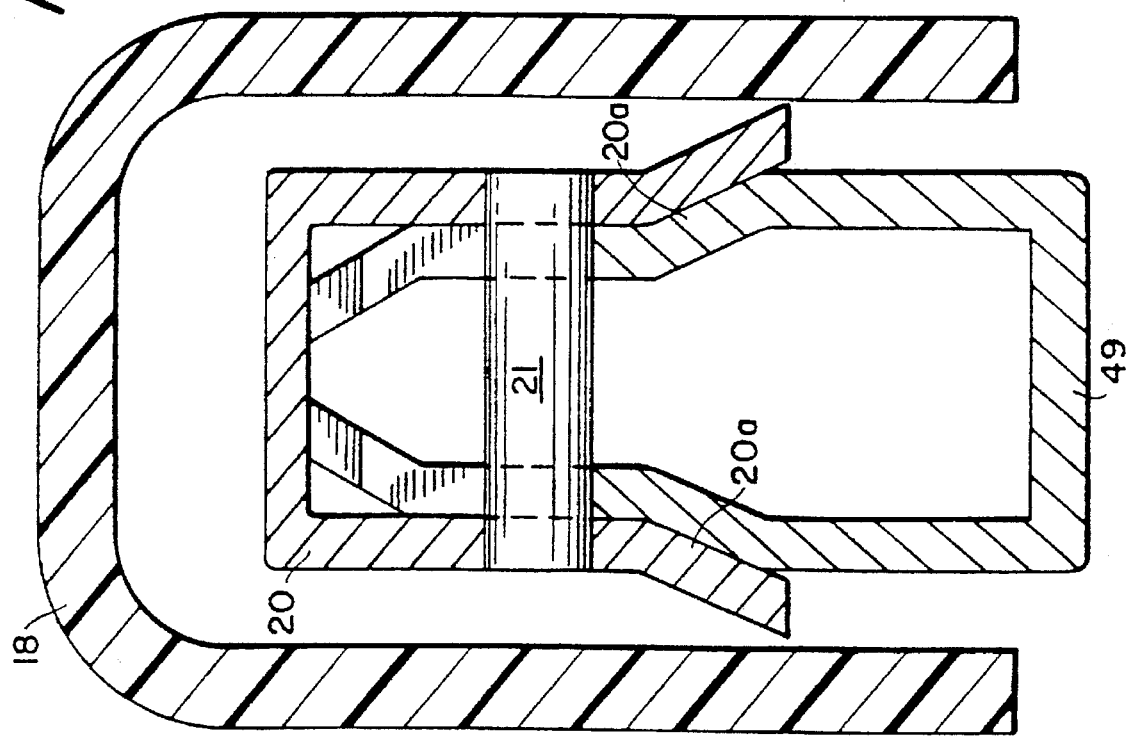
FIG. 9 is a cross-sectional view taken along lines 9—9 of FIG. 6 illustrating one alignment feature of the apparatus at the proximal end.

Referring now further to FIGS. 6, 7 and 8 the finger operated pad and associated mechanism for advancing the tissue cutting knife and fastener closure cam bars are shown. FIG. 6 is a cross-sectional view taken along lines 6—6 of FIG. 1, and FIG. 7 is a cross-sectional view taken along lines 7—7 of FIG. 6. FIG. 8 is a cross-sectional view taken along lines 8—8 of FIG. 6. Finger pad 40 is connected to cam bar retainer 38 by stem 42 with cam bars 34, 36 and knife bar 32 connected at their proximal end portions to bar retainer 38 and retained in their positions by fastener stems 32c, 34b, and 36b having cutout lock tabs 32d, 34c and 36c which engage raised portions in the cam bar retainer 38 as shown in FIG. 7. The proximal end portion 49 of retainer channel 48 has a cut-out portion 49a (FIGS. 4 and 6). A transverse pin 21 is positioned at the proximal end of fastener channel 20 as shown in FIGS. 6 and 9. To assemble the half sections 12 and 14, pin 21 is inserted within cut-out portion 49a of proximal end 49 of retainer channel 48. This facilitates alignment of retainer channel 48 with fastener channel 20 when the half sections 12, 14 of the apparatus are assembled as shown in FIGS. 6 and 9. As shown in FIG. 9, the proximal end portion 49 of fastener channel 48 is inserted snugly between the sidewalls 20a of retainer channel 20 to secure the mating positions of the channels as shown when the half sections 12, 14 are assembled. Further alignment of the half sections 12, 14 of the apparatus is provided by the locking mechanism which will be described hereinbelow.

Figure 2:
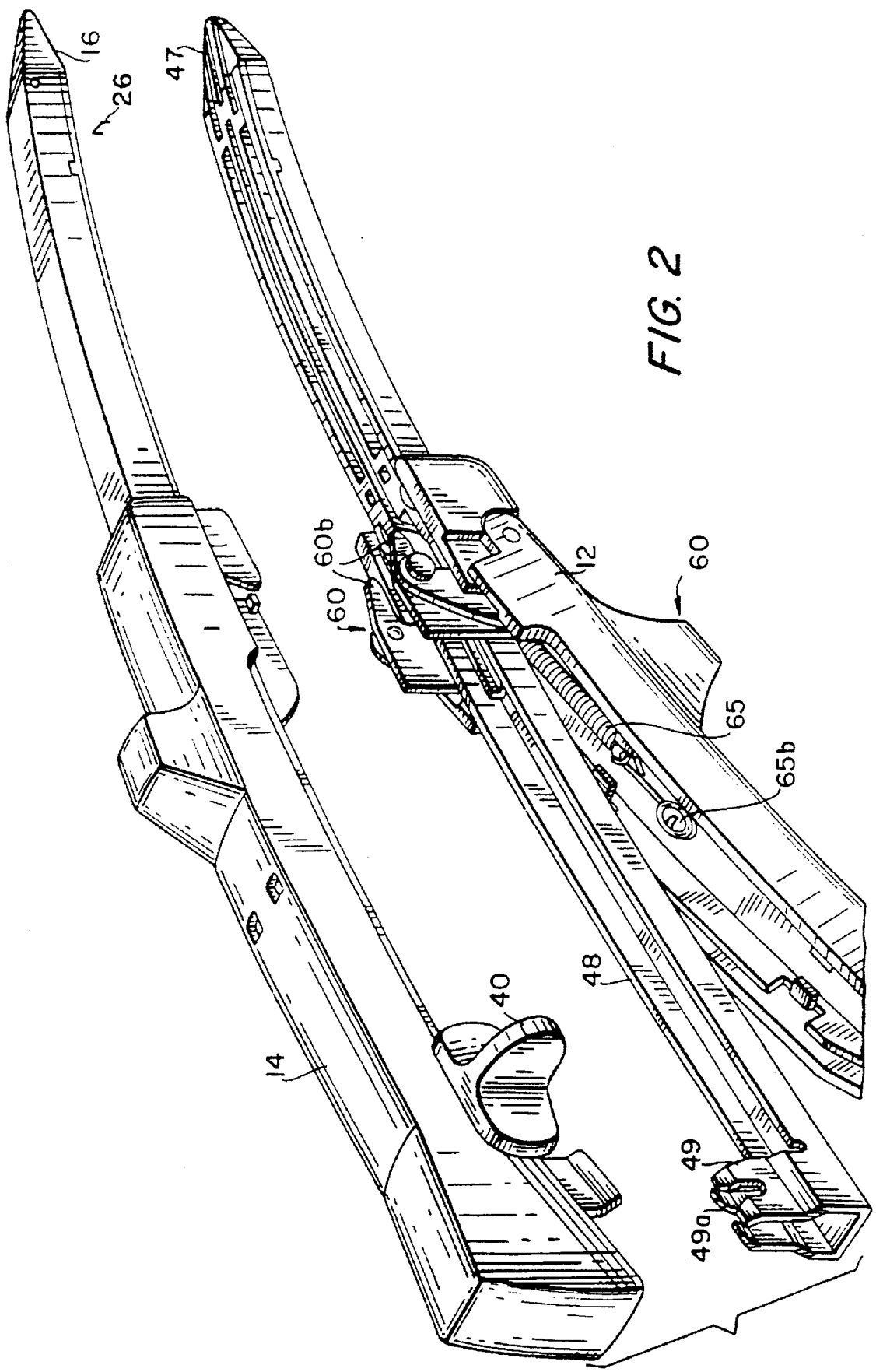
FIG. 2 is an exploded perspective view of the arcuately configured apparatus of FIG. 1, illustrating the two half sections of the fastener applying mechanism.
Figure 13:
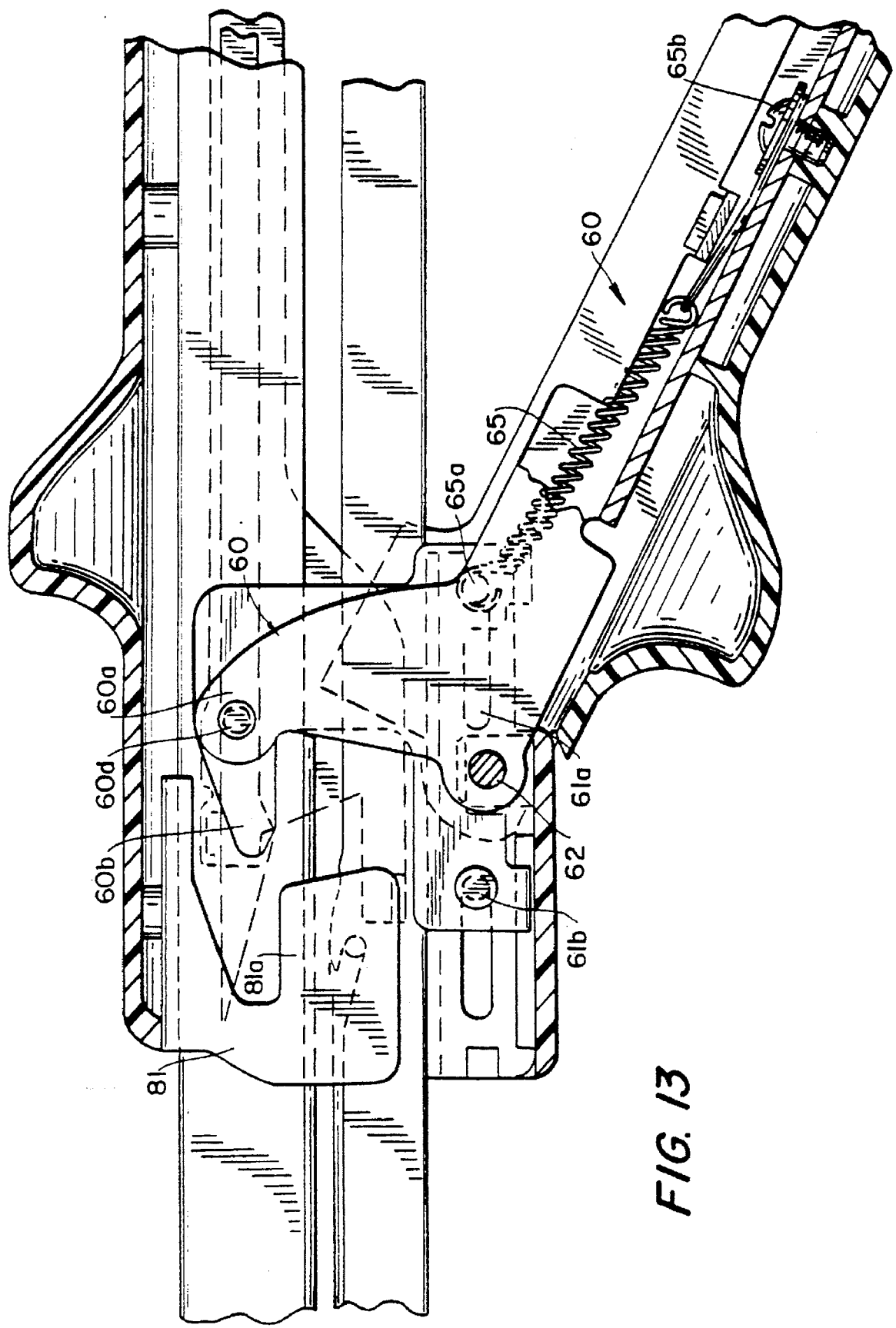
FIG. 13 is a view, partially in cross-section of the portion of the handle section incorporating the clamp mechanism for securing the half sections of the apparatus together for effecting closure.
Figure 15:
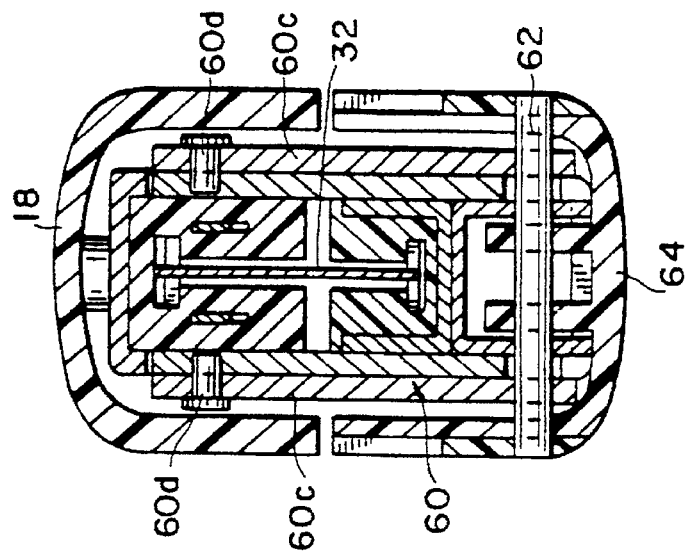
FIG. 15 is a cross-sectional view taken along lines 15—15 of FIG. 14.

Referring now to FIG. 13 in conjunction with FIG. 2, the mechanism for locking the half sections 12,14 is illustrated in cross-section. Handle clamp 60 (shown in FIG. 4) is pivotally mounted to retainer channel 48 by pin 62 as described previously, and includes distal clamp section 60a having locking fingers 60b pivotally attached to body plates 60c by rivets 60d. Clamp 60a is supported by clamp support 61 shown in FIG. 4. These locking fingers are dimensioned and configured to engage shoulders 81a of anchor 81 attached to fastener channel 20 (also see FIG. 3) when the half sections 12, 14 are assembled in face to face relation and handle 64 and clamp 60 are pivotally advanced toward half section 14. This movement causes distal linear movement of body plates 60a and locking fingers 60b to lockingly engage anchor 81 to secure the half sections 12,14 together. This arrangement of articulated components is particularly desirable in view of the curved configuration of the half sections of the apparatus since the curved configuration would otherwise provide difficulty in securing the half sections 12, 14.

Figure 14:
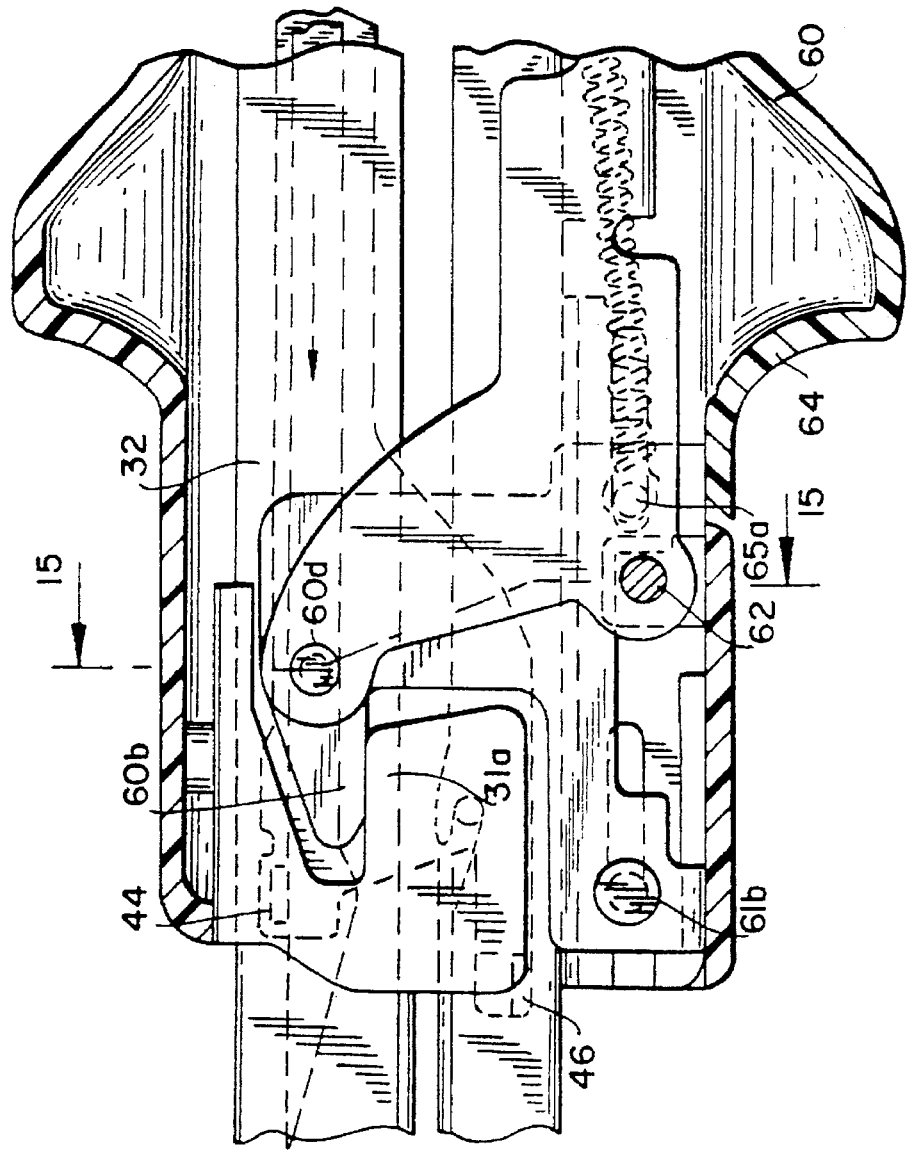
FIG. 14 is a view, partially in cross-section of the handle portion of FIG. 13 with the clamp mechanism in the locked position.

Referring further to FIG. 13, spring 65 is connected at the distal end to cross pin 65a and at the proximal end to screw 65b to bias the clamp 60 toward the open position as it is closed and pin 65a moves distally within slots 61a in clamp support 61. Pin 61b moves distally as shown in FIG. 14 when the clamp is closed. The dimensions of the clamp 60 and anchor 81 are such that the frictional contact force between fingers 60b and shoulders 81a retains the clamp 60 in the closed position against the force of spring 65 when body tissue is gripped between the half sections 12, 14. Biasing clamp 60 toward the open position facilitates quick release after the unlocking movement of the clamp has been started.

Referring now to FIG. 4 in conjunction with FIG. 3, a safety feature of the present apparatus is illustrated. The knife bar 32 includes fastener shoe 44 attached to the distal end portion as shown, and retainer shoe to attached to the distal end portion as shown. When the half sections 12,14 are fully assembled and handle 64 and clamp 60 are closed distal movement of finger pad 40 is made possible, which causes corresponding distal movement of the curved cam bars 34,36 and curved knife bar 32. With this motion, retainer shoe to and fastener shoe 44 slide distally within the arcs defined by the respective channels defined by fastener shoe plate 30 and retainer shoe plate 50. Each shoe plate 30, 50 is generally U-shaped and includes a base 30a, 50a and sidewalls 30b, 50b as shown in FIG. 16 in conjunction with FIGS. 3 and 4. Inwardly extending flanges 30c, 50c extend toward each other across the opening defined by the sidewalls, leaving a narrow gap 50d (FIG. 16) midway between the flanges as shown. It will be readily appreciated that any distal movement of finger pad 40 will be arcuate and will cause the shoes 44, to to enter their respective channels and prevent separation of the half sections 12,14 in the event handle 64 and clamp 60 are inadvertently urged toward the unlocked position. The prevention of such separation is provided by the interference between flanges 30c, 50c and the respective shoe 44, to Continued distal motion results in transverse movement of the fastener pushers to cause sequential closure of the fasteners with the retainers.

Figure 17:
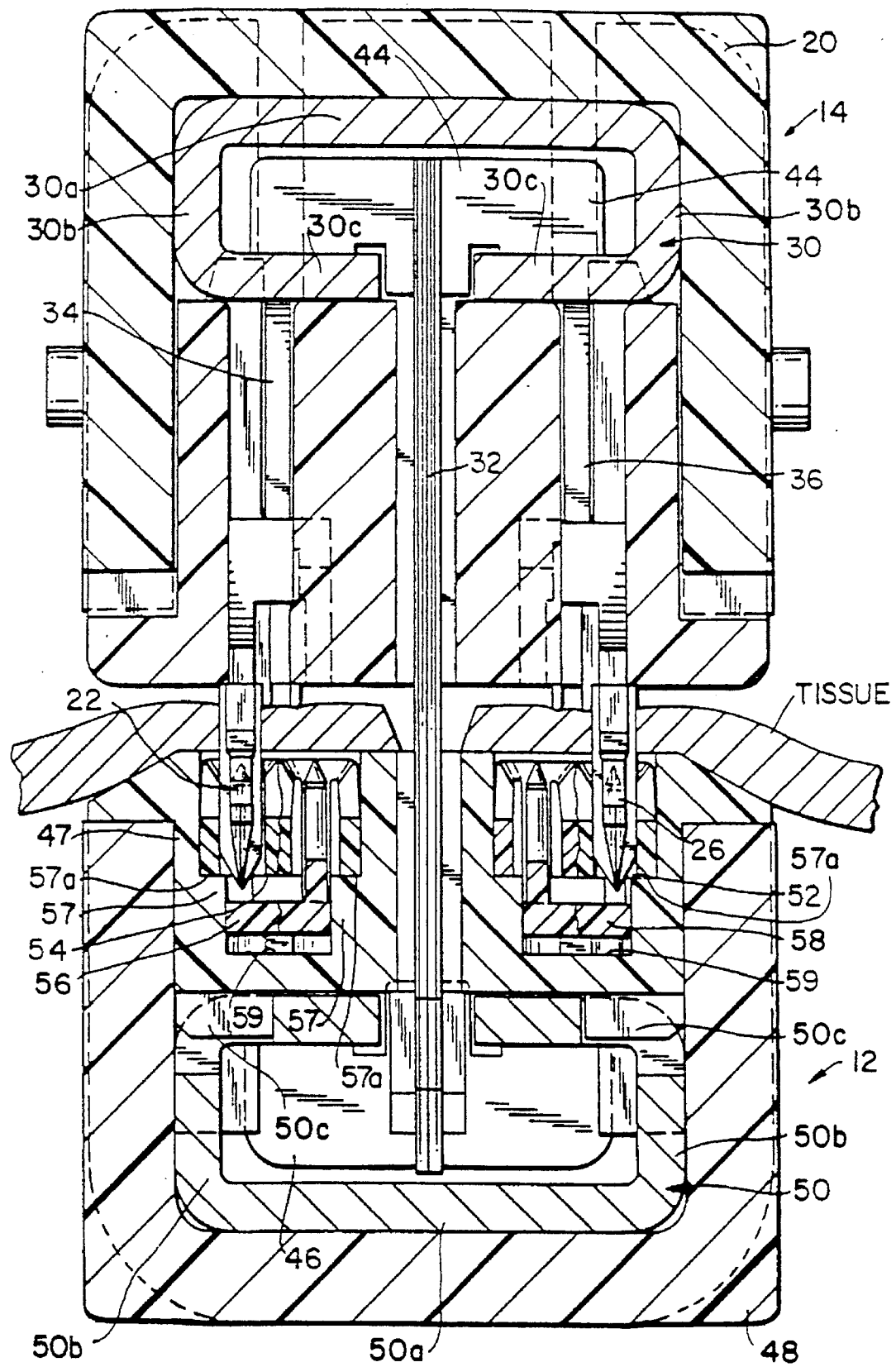
FIG. 17 is a view similar to FIG. 16, illustrating the fasteners and retainers after firing the apparatus.
Figure 18:
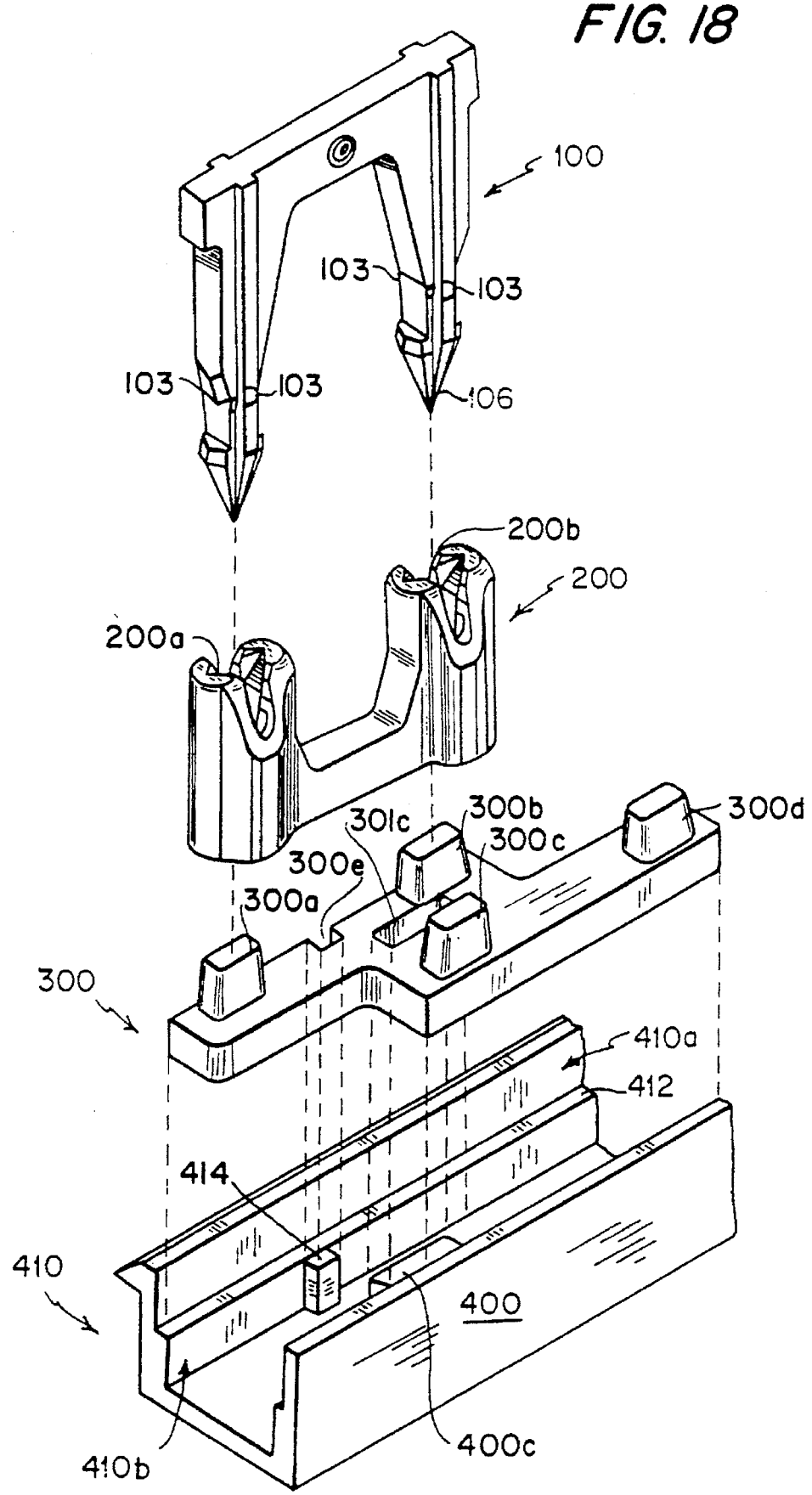
FIG. 18 is a more detailed exploded perspective view of a two-part surgical fastener shown with the retainer mounting element and the arcuately configured retainer holding cartridge of the present invention.
Figure 19A:
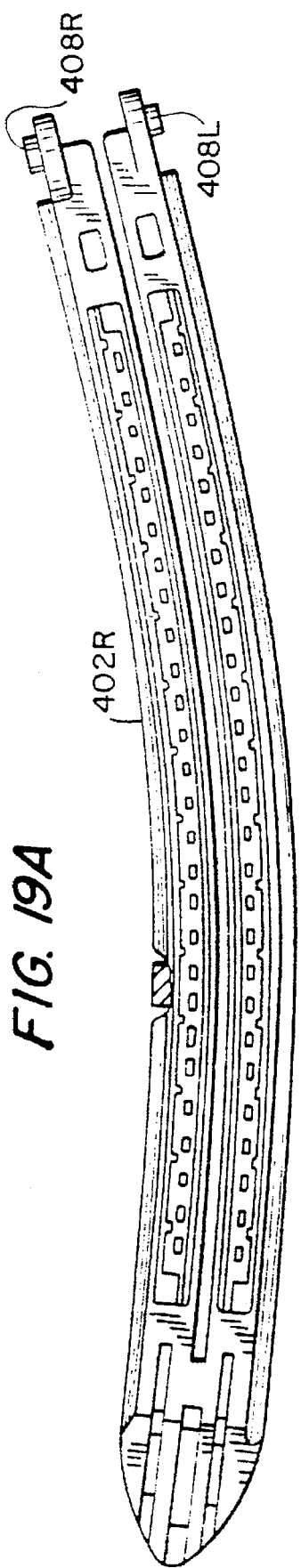
FIGS. 19A, 19B, 19C and 19D are respectively, top plan, side elevational, bottom plan, and cross-sectional views providing further details of the arcuately configured retainer holding cartridge.
Figure 19B:
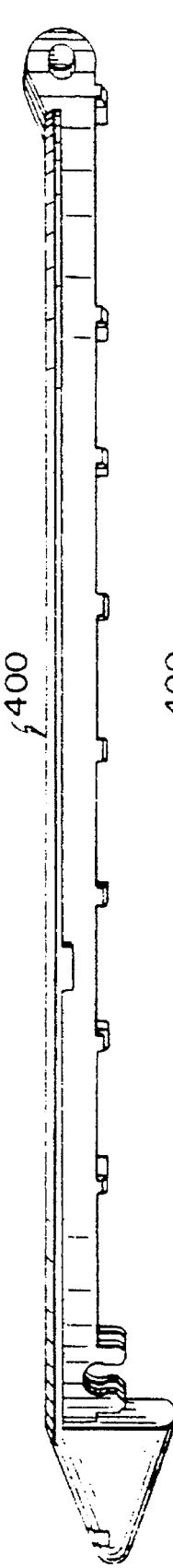
Figure 19C:
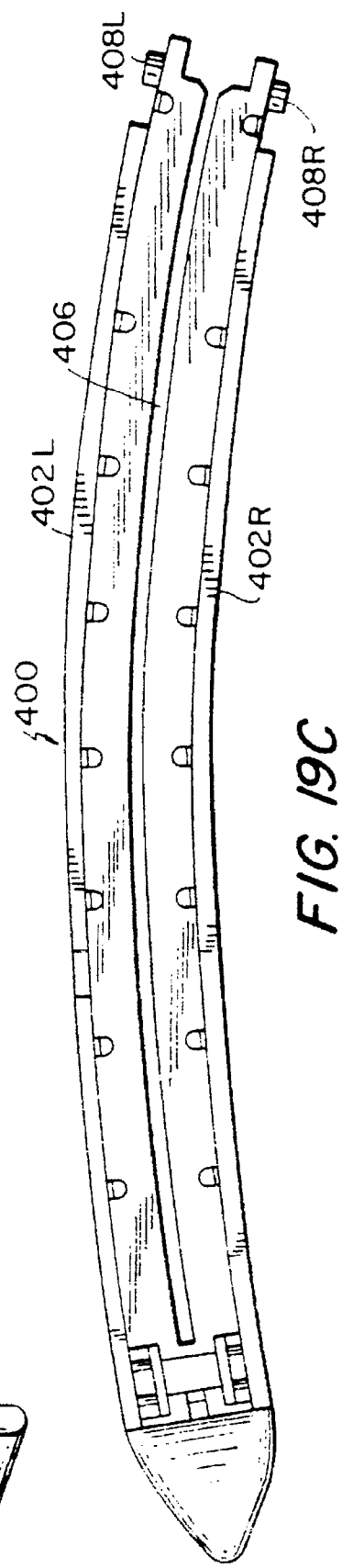
Figure 19D:
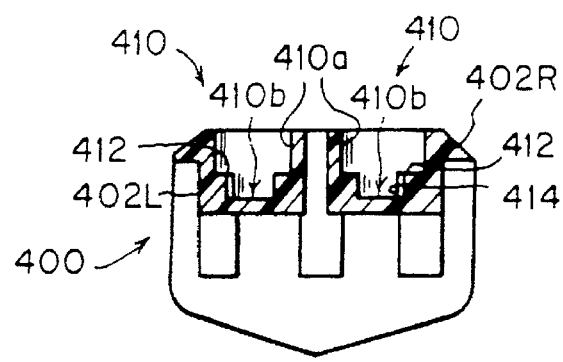

FIG. 16 illustrates the half sections 12,14 in the pre-fired positions and FIG. 17 illustrates the half sections 12, 14 of the apparatus after the fasteners are fired and the tissue is cut. Similarly, FIGS. 18, 19 and 20 illustrate the fastener and retainer system in exploded views. Referring now to FIG. 16 in conjunction with FIGS. 1 and 2, a cross section of the fastener system illustrates fastener half section 14 with exemplary fastener 22 and half section 12 with exemplary retainer 54. Retainer holder 58 secures retainer 54 in precisely correct aligned position by insertion of posts 51 into the apertures of the retainer on the side opposite the fastener entry side. FIG. 17 illustrates the half sections shown in FIG. 16 after moving the finger pad 40 forward, which cause the following simultaneous actions:

1) knife 32a cuts tissue as shown.

2) fastener cam bars 34, 36 sequentially engage fastener pushers 24, 28 causing movement of the fasteners 22, 26 toward retainers 52, 54 such that the fasteners engagably enter the retainer openings and simultaneously push retainer holders 56,58 deeper into the cartridge 50 while releasing the hold which holders 56, 58 previously had on retainers 52,-54. This position causes the resilient spear shaped leading edge of the absorbable two-part fasteners 22,26 to be securely retained within the retainers 52, 54 which are dimensioned and shaped for corresponding locked interference fit with the fasteners. While this fastening action occurs the retainers 52, 54 are supported on surfaces 57a of side shelves—or rails—57 as shown in FIG. 11. Thus, the tissue halves become securely fastened by the dual staggered rows of fasteners on each side of the cut and the organs are joined to form a single hollow chamber.

The downward motion of the fasteners 22, 26 is aligned precisely with the retainer openings due to the alignment of the retainers as secured by the holders 54, 56 and the uniform downward motion provided by the fastener pushers 24, 28. The second (or distal) sloped surface 68b of the same pusher, as shown in FIG. 4, facilitates proximal movement of the curved cam bars 34,36 along the arcs defined by their radii of curvature.

Referring now to FIGS. 18–22, the inventive fastener and retainer system constructed according to the present invention is shown in exploded perspective views providing additional details of the fastener locking systems. For convenience of illustration in connection with these Figures, the numerals of the components shown in FIGS. 12 et seq. are numbered, beginning with 100. Thus, certain elements in these Figures will bear numerals differing from those utilized in the previous Figures.

Referring to FIG. 18, fastener 100 has a spear shaped tip 106 dimensioned for forced entry into apertures 200a and 200b of retainer 200. Bumps 103 help to retain fastener 100 within retainer 200 after entry has been completed. In FIG. 18 raised bumps 103 are shown at two locations. Raised bumps 103 are also provided on the rear face of fastener 100 (not shown) to retain the fastener. Retainer 200 is securely positioned on retainer holder 300 having upstanding posts 300a, 300b, 300c, 300d which are dimensioned and configured to enter apertures 200a and 200b of retainers 200 on the side opposite the fastener entry side. The retainer holder 300 provides a stable flat base for the retainer and disengages from the retainer when the fastener portion engages the retainer. As noted hereinabove, during the operation of the instrument the fasteners are ejected from the fastener holding cartridge to mate with their respective retainers. Further details of novel retainer holding cartridge 400 may be seen by referring to FIGS. 19a, 19b, 19c and 19d.

Retainer holding cartridge 400 is an elongated arcuately shaped piece having two members 402L and 402R longitudinally extending proximally from the distal end 404 of the retainer holding cartridge 400. Left and right members 402L and 402R define a center longitudinal slot 406 for receiving the distally moving knife member 32 described hereinabove. In one embodiment, the proximal ends of members 402L and 402R have outwardly projecting pins 408L and 408R respectively, for pivotally mounting to a surgical fastener applying instrument. Alternatively, these pins could be eliminated- Each member 402L and 402R has a compartment 410 (See FIG. 18) comprising a relatively wide upper vertical walled channel 410a for seating one or more retainers, and a relatively narrow lower vertical walled channel 410b for mounting the retainer mounting elements. The difference in widths between the upper and lower channels defines shelves 412 on both sides of the compartment which support the retainers and act as a backstop. The lower channel 410b is adapted to hold retainer holders 300 in a frictional fitting such that they are frictionally supported in an initial upper position wherein the retainer holders 300 are engaged with the retainers 200. The retainer holders 300 may be slightly curved along their sides to match the curvature of the cartridge 400 so as to be downwardly slidable when forced out of engagement with the retainers 200 by the entering prongs of the fastener portions 100. Depending upon relative dimensions, the retainer holders, being extremely small in comparison to the cartridge, may be of straight construction along their sides.

Vertical guide rails 414 on the sides of the channels cooperate with slots 300e formed in retainer holder 300 to reduce the unwanted torquing of the retainer holders 300 and prevent the retainer holders 300 from moving distally or proximally. In the alternative, vertical post 400c may be provided to engage an aperture 301c in the retainer holder 300. See, also, post 51 engaging aperture 53 as shown in FIG. 5. Alternatively, the retainer cartridge 400 could be provided with both a vertical guide rail 414 on each side to engage a respective side slot 300e in retainer holder 300, and a central post 400C as shown in FIG. 18 dimensioned to be received in aperture 301C in retainer holder 300.

Figure 20A:
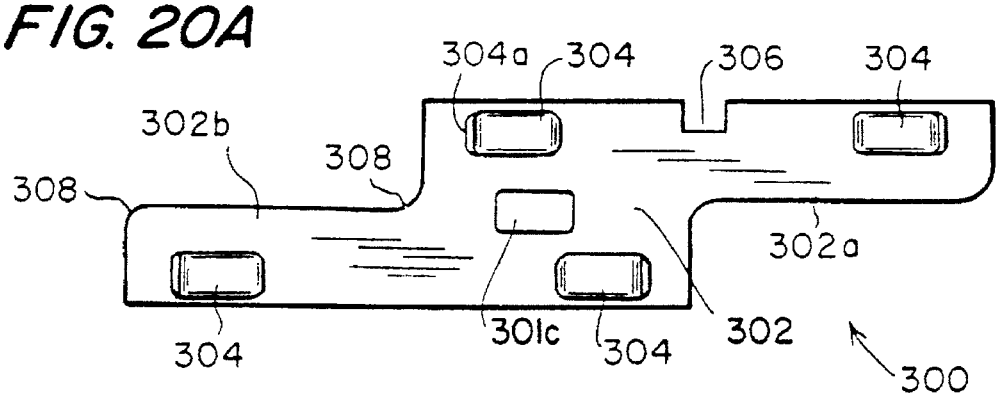
FIGS. 20A and 20B are top plan views of left hand, and right hand retainer mounting elements, respectively.
Figure 20B:
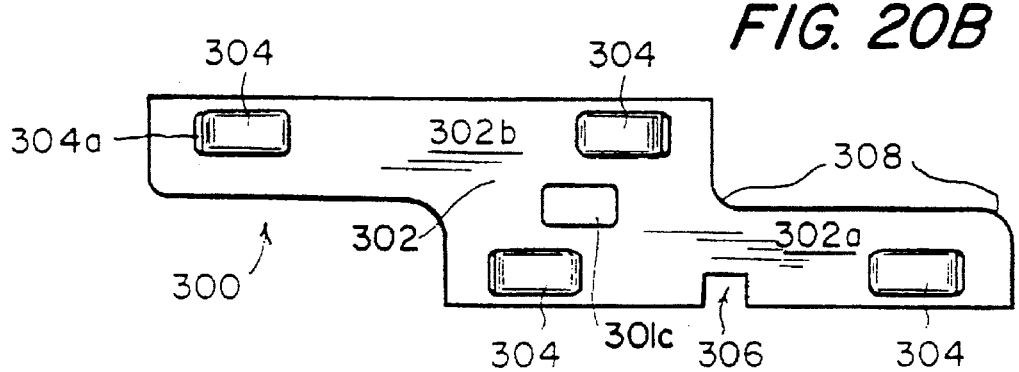
Figure 20C:
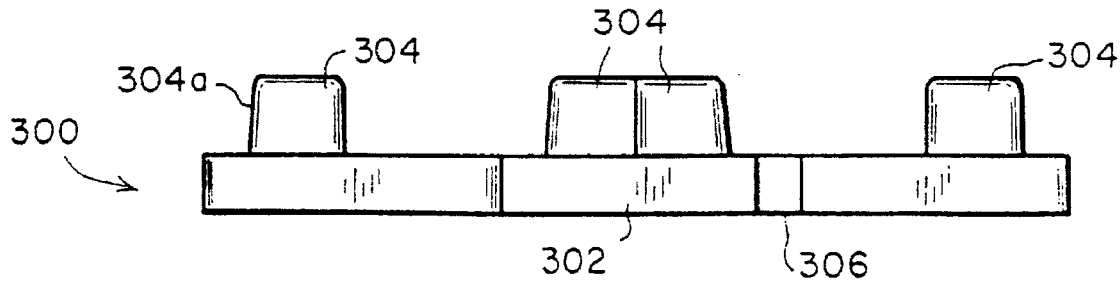
FIG. 20C is a side elevational view of the retainer mounting element of FIG. 20B.

Referring now to FIGS. 20A, 20B and 20C, further details of the retainer holders are shown. As noted, the retainer holders may have curved sidewalls to match the curved sidewalls of the cartridge 400 or they may be straight, depending upon the relative dimensions of the components. Retainer holder 300 includes a base 302 having two integrally connected substantially rectangular portions 302a and 302b, and a plurality of upright posts 304 for entry into the apertures on the bottom portion of the retainer as described hereinabove. The base has a vertical notch 306 for slidably engaging guide rails 414 of the retainer cartridge 400. Rounded corners 308 enable a smoother sliding fit between the convex corner of one retainer mounting element being adapted to fit into the concave corner of another mounting element. As noted, the width of base 302 is such that the retainer mounting element 300 is retained in the lower channel 410b by friction, or slight interference fit, although the retainer mounting element 300 is slidable in the vertical direction. The upright posts 304 ideally each have a sloped side 304a which is angled slightly off the vertical such that the top of the upright post is slightly narrower than the bottom. The tapering facilitates the entry and removal of the upright posts from the retainer apertures.

Figure 21B:
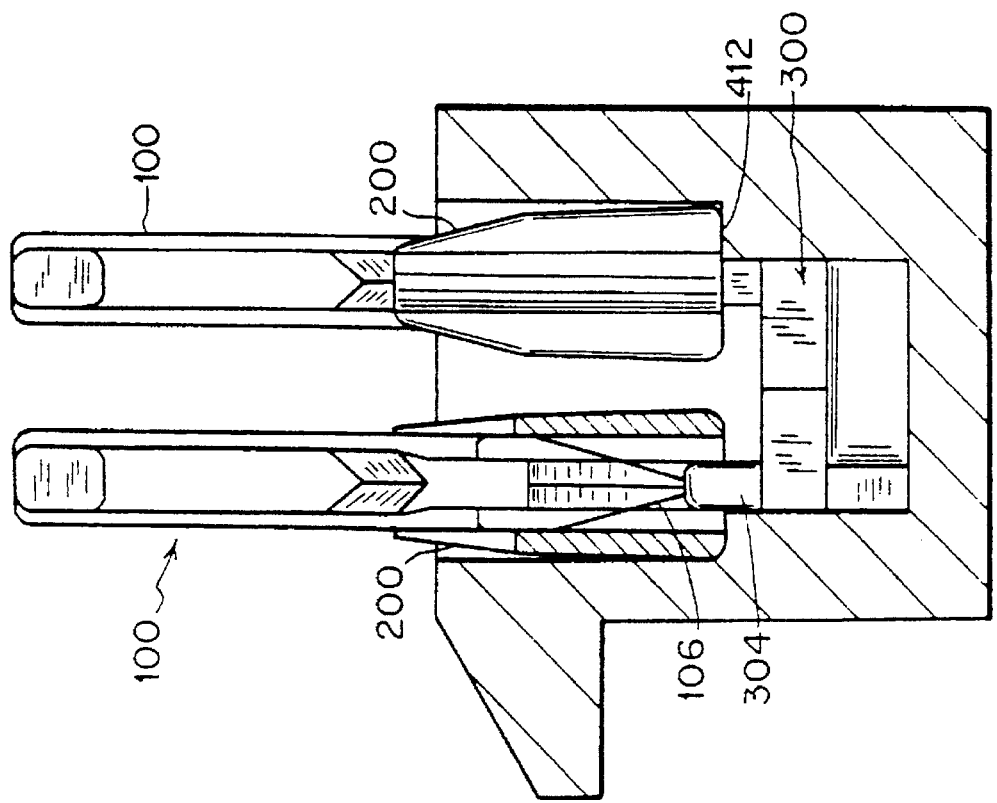
FIG. 21B illustrates in cross-sectional view, the retainer portion of a two-part surgical fastener positioned on a mounting element in the fired position.
Figure 21A:
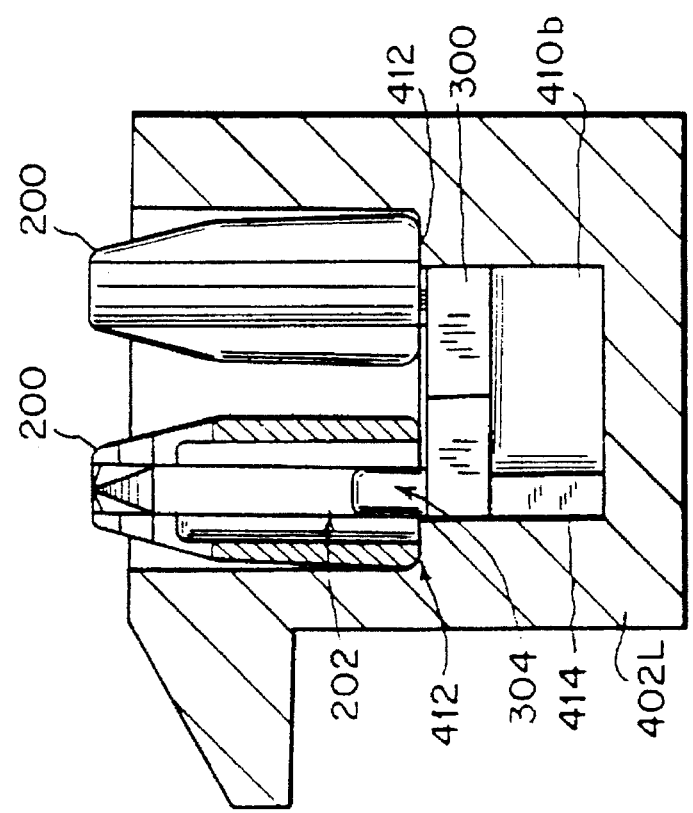
FIG. 21A illustrates in cross-sectional view, further details of the retainer portion of a two-part surgical fastener positioned on a retainer mounting element in the pre-fired position.

Referring now to FIGS. 21A, 21B and 22, the retainers 200 are initially in the position illustrated in FIG. 21A. The retainer 200 is located in the upper chamber 410a, and mounted on retainer holder 300 by means of upright or posts 304 which are inserted into the apertures 202 at the bottom of the retainer 200. A portion of the bottom of the retainer 200 overlaps the edge of base 302 such that the overlapping portion rests on shelf 412.

Retainer holder 300 is slidably mounted within the lower channel 410b of the arcuate cartridge 400 with notch 306 in engagement with guide rail 414.

When the fasteners 100 are inserted into retainers 200, the barbed tips 106 of the fasteners push down on the upright posts 304, thereby pushing the retainer mounting element 300 down into a position where it is no longer in engagement with the retainer 200. The retainers 200 are critically dimensioned and configured to be supported by shelves 412 such that they are braced against downward movement. Upon disengagement with the retainer holders 300, the retainers 200 are free to be lifted out of the cartridge 400 in engagement with the fasteners.

FIG. 22 illustrates in further detail, the operative portion of the apparatus for applying surgical fasteners, employing the fastener and cartridge system of the present invention as described hereinabove. The fastener holding cartridge 500 contains fastener pushers 502, cam bar 504, and optionally a knife 506. When actuated, the cam bar 504 is moved distally, thereby contacting the sloped camming surface 502a of pusher elements 502 and urging the fastener portions downward into the retainer cartridge 400 where fastener 100 engages its respective retainer 200. As described above, the cam bar 504 operates upon the pusher elements 502 sequentially, first contacting the proximal end of each pusher element. As noted, because of this movement there may be a tendency for unwanted torque to develop which might otherwise cause a relative clockwise pivoting of the fastener. Flat mounting element bases 302 and shelves 412 help insure that the retainers 200 do not pivot appreciably.

In use, the apparatus is positioned such that a layer of body tissue is situated between the fastener holding cartridge 500 and the retainer holding cartridge 400. The curvature of the apparatus facilitates insertion into body areas requiring such fastening such as is required for colon anastomosis, tubal ligations, vaginal hysterectomies and related surgical procedures. When the apparatus is actuated the fastener barbs 106 will penetrate the tissue layer and lock into the retainer 200, thereby sealing the tissue. Although FIG. 17 shows the fasteners 100 moving downwardly, the direction of movement to engage retainer 200 will obviously depend upon the orientation of the apparatus during use.

Figure 23:
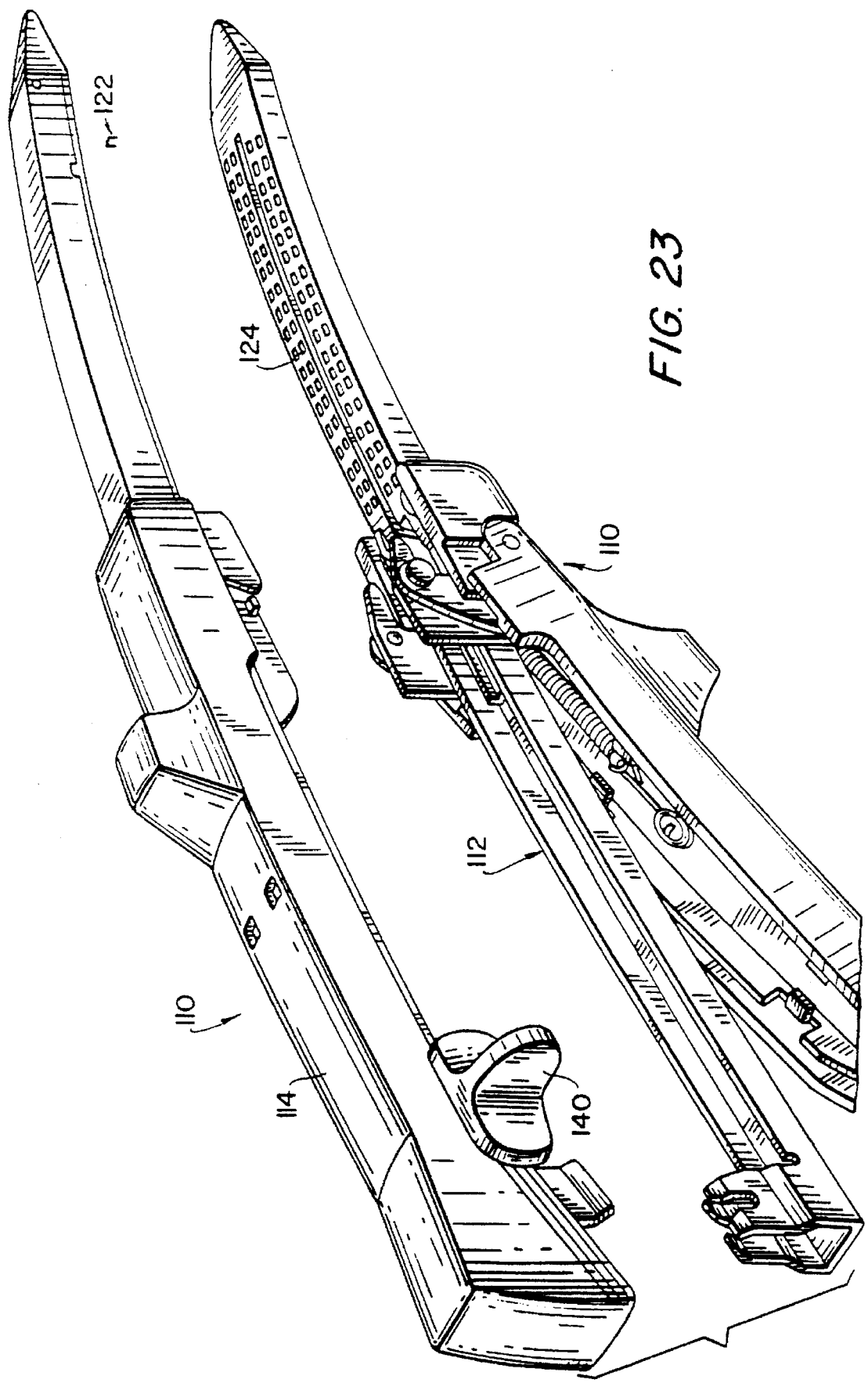
FIG. 23 is a perspective view of an alternative embodiment of the present invention adapted for firing staples which are closed by engagement with a correspondingly positioned anvil half section.

FIG. 23 illustrates an alternative embodiment of the invention wherein the fasteners are metal staples having a base member and two legs extending perpendicular to the base member as shown at 122 for example, and the closure member includes a series of anvils 124 effecting closure by engagement of the leg members with the anvils. Curved apparatus 110 is formed of fastener half section 114 and anvil half section 112.

The apparatus as described hereinabove is preferably constructed as a disposable apparatus suitable for a single use. However, the apparatus is readily adaptable to a multiple use or non-disposable form merely by structuring the fastener and retainer cartridges so as to be replaceable within their respective channels. In such case, replacement of the curved knife bar 32 with knife blade 35 is also desirable in order to assume precise and accurate cutting of the tissue. The curved cam bars 34,36 could also be replaceable along with curved knife 32. In the preferred form, the components are constructed of steel except for the cartridges and the finger pad 40, which are constructed of a suitable plastic material such as nylon or polycarbonate. The preferred fastener and retainer are composed of a bioabsorbable polymeric material, such as polymers or copolymers of glycolide, lactide, p-dioxanone, polyester, polyamino acids and the like, the preferred construction of which is shown and described in U.S. Pat. No. 4,932,960, which is hereby incorporated by reference.

What is claimed is:

1. Apparatus for applying at least one row of surgical fasteners, including a frame portion having a handle and an arcuate tissue holding portion extending from the handle, which comprises:
   a) first arcuate means disposed on the tissue holding portion for holding said fasteners in at least one row;
   b) second arcuate means disposed on the tissue holding portion configured and dimensioned to cooperate with said first arcuate fastener holding means to position tissue between the first and second arcuate means; and
   c) fastener driving means slidably disposed on said handle and slidably extending into said first arcuate means for driving said fasteners sequentially along said row into tissue from said first arcuate means toward said second arcuate means.

2. The apparatus of claim 1 wherein said fastener holding means is a fastener cartridge.

3. The apparatus of claim 2 wherein said fasteners are two-part fasteners, including a first fastener portion positioned in said fastener cartridge and a second retainer portion supported by said second arcuate means.

4. The apparatus of claim 2, wherein said second arcuate means includes an anvil surface positioned thereon and adapted to crimp said fasteners.

5. The apparatus of claim 3 wherein said fastener portions and said retainer portions are arranged in alignment with a central arcuate axis.

6. The apparatus of claim 3 wherein said retainer portions are supported by a corresponding plurality of retainer mounting elements positioned in said second arcuate means.

7. The apparatus of claim 6 wherein said second arcuate means includes a retainer cartridge for supporting said retainer portions.

8. The apparatus of claim 7 further comprising means to cut tissue adjacent the location of application of said fasteners.

9. The apparatus of claim 8 wherein said retainer mounting elements are slidably mounted within at least one channel in said retainer cartridge.

10. The apparatus of claim 9 wherein said retainer mounting elements release their respective retainer portions in response to the engagement of the fastener portions with their respective retainer portions.

11. The apparatus of claim 10 wherein said retainer mounting elements each comprise a base portion and at least one upright post for engaging an aperture in said retainer portion and frictionally holding said retainer.

12. The apparatus of claim 11 wherein said driving means sequentially drives said fastener portions of said two-part fasteners into engagement with their respective opposed retainer portions.

13. The apparatus of claim 3 wherein said two-part fasteners are bio-absorbable.

14. Apparatus for applying at least one row of two-part surgical fasteners to body tissue, including a frame portion having a handle and an arcuate tissue holding portion extending from the handle, each surgical fastener having a pronged fastener portion and a retainer dimensioned and configured to receive the pronged fastener portion into engaged relation therewith, which comprises:
   a) an arcuately configured fastener holding member disposed on the tissue holding portion and adapted for releasably holding a plurality of said fastener portions;
   b) retainer holding means disposed on the tissue holding portion in opposed relation to and spaced from said fastener holding member for releasably holding a plurality of said retainers in positions opposite said respective fastener portions, said retainer holding means being arcuately configured corresponding to said fastener holding member, the fastener holding member and the retainer holding means being adapted to hold tissue therebetween; and
   c) means disposed on said handle for sequentially advancing each of said fastener portions toward said retainers so as to cause said fastener portions to engage said retainers while fastening body tissue therebetween.

15. The apparatus of claim 14 wherein said arcuately configured member for holding fastener portions comprises a fastener cartridge attached to an arcuate channel member.

16. The apparatus of claim 15 wherein said fastener cartridge is permanently attached to said channel member.

17. The apparatus of claim 15 wherein said fastener cartridge is removably attached to said channel member.

18. The apparatus of claim 17 wherein said arcuately configured means for holding retainers includes a retainer cartridge attached to an arcuately configured channel member.

19. The apparatus of claim 18 wherein said retainer cartridge is permanently attached to said channel member.

20. The apparatus of claim 18 wherein said retainer cartridge is removably attached to said channel member.

21. Apparatus for applying at least two rows of two-part surgical fasteners to body tissue and for cutting the body tissue, each said surgical fastener having at least a two pronged fastener portion for piercing body tissue, and a retainer member dimensioned and configured to receive said fastener portion in engaged relation such that the fastener portion and the retainer member are respectively positioned on opposite sides of the body tissue, which comprises:
   a) a two-part frame having handle portions and separable arcuately configured sections extending from the handle portions, the handle portions and arcuately configured sections being capable of releasable attachment to each other, the arcuately configured sections each defining an elongated finger portion;
   b) a fastener carrying cartridge having an arcuate configuration similar to one of said elongated finger portions and mounted along one of said finger portions and carrying a plurality of said fastener portions;
   c) a retainer carrying cartridge having an arcuate configuration similar to the other of said elongated finger portions and mounted along said other finger portion opposite said fastener cartridge and carrying a plurality of said retainer members positioned opposite said fastener portions, each said retainer member having apertures dimensioned and positioned for reception of pronged portions of said fastener portions when said fastener portions are advanced toward said retainer members;
   d) means mounted on said handle portions of said frame for sequentially advancing said fastener portions toward said retainer members while piercing body tissue positioned therebetween to effect application of said two-part fasteners to the body tissue; and e) means to cut body tissue adjacent the location of application of said fasteners.

22. The apparatus of claim 21 wherein said two-part frame comprises a pair of channel members having means to releasably attach said members in face to face relation.

23. The apparatus of claim 22 wherein said fastener cartridge comprises two pairs of rows of staggered apertures dimensioned and configured for frictionally holding a plurality of said fastener portions, and fastener pusher members associated with said apertures to push said fastener portions from said cartridge in response to movement of said fastener advancing means.

24. The apparatus of claim 23 further comprising a plurality of retainer holders positioned in said retainer cartridge, said holders having means to support said retainer members in position for reception of said fastener portions.

25. The apparatus of claim 24 further comprising a pair of cam bars positioned for slidable movement distally and proximally within said frame for sequential engagement with said fastener pushers, said cam bars being dimensioned and configured to sequentially advance said fastener pushers toward said fastener portions to effect engagement of said fastener portions with said retainer members.

26. The apparatus of claim 25 wherein each said fastener pushers has dual oppositely sloped surfaces.

27. The apparatus of claim 26 wherein a handle is positioned at the proximal end of said frame.

28. The apparatus of claim 27 wherein said fastener holding and retainer holding cartridges curve to the left from said handle to the distal end of said frame.

29. Apparatus for applying at least one row of two-part surgical fasteners, including a frame portion having a handle and an arcuate tissue holding portion extending from the handle, each surgical fastener having a pronged fastener portion and a retainer, which comprises:
  a) arcuate means disposed on the tissue holding portion for holding said fastener portions of said two-part surgical fasteners;
  b) arcuately configured retainer cartridge disposed on the tissue holding portion having means for holding a plurality of retainers in positions opposite said fastener portions, the fastener holding means and the retainer cartridge being adapted to hold tissue therebetween;
  c) a plurality of retainer mounting elements located in said arcuately configured retainer cartridge for releasably engaging and holding said retainers; and
  d) driving means for sequentially driving said fastener portions of said two-part fasteners through tissue and into engagement with their respective opposed retainers.

30. Apparatus for applying at least one row of surgical fasteners including a frame portion having a handle and an arcuate tissue holding portion extending from the handle, which comprises:
  a) first arcuate member disposed on the tissue holding portion for holding at least one row of fasteners;
  b) second arcuate member disposed on the tissue holding portion configured and dimensioned to cooperate with the first arcuate fastener member to hold tissue therebetween;
  c) a fastener driver slidable along an arcuate path through said tissue holding portion for sequentially driving the fasteners along the row into tissue from the first arcuate member toward the second arcuate member; and
  d) a slidable control member disposed on said handle for advancing said fastener driver.

31. The apparatus of claim 30 wherein the first arcuate fastener holding member comprises a fastener cartridge.

32. The apparatus of claim 31 wherein the fasteners are two-part fasteners, a fastener portion positioned in the fastener cartridge and a retainer portion supported by the second arcuate member and adapted to become engagably attached to the fastener portions.

33. The apparatus of claim 31 wherein the second arcuate member includes an anvil surface positioned thereon and adapted to crimp the fasteners.

34. The apparatus of claim 32 wherein the fastener portions and the retainer portions are arranged in alignment with a central arcuate axis.

35. The apparatus of claim 32 wherein the retainer portions are supported by a corresponding plurality of retainer mounting elements positioned in the second arcuate member.

36. The apparatus of claim 35 wherein the second arcuate member comprises a retainer cartridge for supporting the retainer portions.

37. The apparatus of claim 36 further comprising a knife blade to cut tissue adjacent the location of application of the fasteners.

38. The apparatus of claim 37 wherein the retainer mounting elements are slidably mounted within at least one channel in the retainer cartridge and the retainer mounting elements release their respective retainer portions in response to the engagement of the fastener portions with their respective retainer portions.

39. The apparatus of claim 32 wherein the two-part fasteners are bio-absorbable.

40. The apparatus of claim 30 wherein the fastener driver includes at least one cam bar slidable longitudinally to sequentially drive the fasteners.

41. The apparatus of claim 32 wherein the fastener driver includes pair of cam bars positioned for slidable movement distally and proximally within the first arcuate member for sequential engagement with fastener pushers, the cam bars being dimensioned and configured to sequentially advance the fastener pushers toward the fastener portions to effect engagement of the fastener portions with the retainer members.

42. The apparatus of claim 41 wherein each said fastener pusher has dual oppositely sloped surfaces.

43. The apparatus of claim 42 wherein a handle is positioned at the proximal end.

44. Apparatus for applying at least one row of two-part surgical fasteners, including a frame having a handle portion and an arcuate tissue holding portion extending from the handle, each surgical fastener having a pronged fastener portion and a retainer, which comprises:
  a) first arcuate means disposed on the tissue holding portion for holding the fastener portions of the two-part surgical fasteners;
  b) second arcuately configured member positioned on the tissue holding portion opposite the first arcuate means, the first means and the second member adapted to hold tissue therebetween; and
  c) driving means disposed on said handle portion and slidable along an arcuate path into said tissue holding portion for sequentially driving the fastener portions of the two-part fasteners from the first means into engagement with their respective opposed retainers on the second means through tissue position in said tissue holding portion.

45. The apparatus of claim 44 wherein the second arcuately configured member is configured for holding a plurality of retainers.

46. The apparatus of claim 44 wherein the driving means includes at least one elongated cam bar.

47. Apparatus for applying at least one row of surgical fasteners, including a frame portion having a handle and an arcuate tissue holding portion extending from the handle, which comprises:
- a) a first arcuate fastener cartridge disposed on the tissue holding portion for holding said fasteners in at least one row;
- b) second arcuate means disposed on the tissue holding portion configured and dimensioned to cooperate with said first arcuate fastener cartridge to position tissue between the first arcuate cartridge and the second arcuate means; and
- c) driving means disposed on the handle and being slidable from the handle into the tissue holding portion for driving said fasteners into tissue from said first arcuate cartridge toward said second arcuate means;

wherein said fasteners are two-part fasteners, including a first fastener portion positioned in said fastener cartridge and a second retainer portion supported by said second arcuate means.

* * * * *